(12) United States Patent
Rapoport et al.

(10) Patent No.: US 10,794,975 B2
(45) Date of Patent: Oct. 6, 2020

(54) RF SHIELDING CHANNEL IN MRI-INCUBATOR'S CLOSURE ASSEMBLY

(71) Applicant: Aspect Imaging Ltd., Shoham (IL)

(72) Inventors: Uri Rapoport, Moshav Ben Shemen (IL); Itzhak Rabinovitz, Gan Yavne (IL); Shmuel Azulay, Tel Aviv (IL)

(73) Assignee: ASPECT IMAGING LTD., Shoham (IL)

( * ) Notice: Subject to any disclaimer, the term of this patent is extended or adjusted under 35 U.S.C. 154(b) by 374 days.

(21) Appl. No.: 15/457,546

(22) Filed: Mar. 13, 2017

(65) Prior Publication Data
US 2017/0181912 A1   Jun. 29, 2017

Related U.S. Application Data

(63) Continuation-in-part of application No. 14/539,442, filed on Nov. 12, 2014, now Pat. No. 10,426,376, and
(Continued)

(51) Int. Cl.
*A61G 11/00* (2006.01)
*G01R 33/422* (2006.01)
(Continued)

(52) U.S. Cl.
CPC .......... *G01R 33/422* (2013.01); *A61B 5/0033* (2013.01); *A61B 5/0555* (2013.01);
(Continued)

(58) Field of Classification Search
CPC ................ A61G 11/005; A61G 11/009; A61G 2210/50; A61B 5/0033; A61B 2503/045;
(Continued)

(56) References Cited

U.S. PATENT DOCUMENTS

| 1,900,342 A | 3/1933 | Hess |
| 2,708,927 A | 5/1955 | Dixon |

(Continued)

FOREIGN PATENT DOCUMENTS

| CA | 2815746 | 5/2012 |
| CN | 2448344 | 9/2001 |

(Continued)

OTHER PUBLICATIONS

Eberich et al., Functional MRI in neonates using neonatal head coil and MR compatible incubator, NeuroImage 20 (2003) 683-692.
(Continued)

*Primary Examiner* — Navin Natnithithadha
*Assistant Examiner* — Sunita Reddy
(74) *Attorney, Agent, or Firm* — Loeb & Loeb LLP

(57) ABSTRACT

A neonate incubator for positioning a neonate within a magnetic resonance imaging (MRI) device is provided. The neonate incubator can include RF shielding that can provide RF shielding during imaging, for example, while life support tubes are connected to the neonate during MRI imaging. The RF shielding can include a door to mate with a bore of the MRI device to provide the RF shielding, and a RF channel that extends along an axis that is substantially parallel to a longitudinal axis of the neonate incubator from an interior chamber of the neonate incubator through the RF shielding door.

15 Claims, 10 Drawing Sheets

Related U.S. Application Data a continuation-in-part of application No. 15/424,428, filed on Feb. 3, 2017, which is a continuation of application No. 13/233,515, filed on Sep. 15, 2011, now Pat. No. 9,597,246.

(60) Provisional application No. 61/905,221, filed on Nov. 17, 2013, provisional application No. 61/383,349, filed on Sep. 16, 2010.

(51) Int. Cl.
  *A61B 5/055* (2006.01)
  *A61B 5/00* (2006.01)

(52) U.S. Cl.
  CPC ...... *A61G 11/005* (2013.01); *A61B 2503/045* (2013.01); *A61G 11/009* (2013.01); *A61G 2210/50* (2013.01); *Y10T 29/49771* (2015.01)

(58) Field of Classification Search
  CPC . A61B 5/0555; A61B 5/055; Y10T 29/49771; G01R 33/422
  USPC .......................... 600/21, 22, 410; 29/407.05
  See application file for complete search history.

(56) References Cited

U.S. PATENT DOCUMENTS

| | | | |
|---|---|---|---|
| 3,012,836 A | 12/1961 | Smith | |
| 3,315,671 A | 4/1967 | Creelman | |
| 3,470,866 A | 10/1969 | Gittelson | |
| 3,655,178 A | 4/1972 | Vezina | |
| 4,161,172 A | 7/1979 | Pickering | |
| 4,543,959 A | 10/1985 | Sepponen | |
| 4,567,894 A | 2/1986 | Bergman | |
| 4,613,820 A | 9/1986 | Edelstein et al. | |
| 4,651,099 A | 3/1987 | Vinegar et al. | |
| 4,712,263 A | 12/1987 | Pronzinski | |
| 4,875,485 A | 10/1989 | Matsutani | |
| 4,936,824 A | 6/1990 | Koch | |
| 4,968,961 A | 11/1990 | Miyajima et al. | |
| 5,028,872 A | 7/1991 | Nakabayashi | |
| 5,059,906 A | 10/1991 | Yamanaka | |
| 5,100,375 A | 3/1992 | Koch | |
| 5,153,546 A | 10/1992 | Laskaris | |
| 5,346,022 A | 9/1994 | Krivec | |
| 5,372,137 A | 12/1994 | Wong et al. | |
| 5,436,607 A | 7/1995 | Chari et al. | |
| 5,446,934 A | 9/1995 | Frazier | |
| 5,565,831 A | 10/1996 | Dorri et al. | |
| 5,759,149 A | 6/1998 | Goldberg | |
| 5,797,833 A | 8/1998 | Kobayashi | |
| 5,800,335 A | 9/1998 | Koch | |
| 5,883,558 A | 3/1999 | Laskaris et al. | |
| 5,917,324 A | 6/1999 | Leussler | |
| 5,971,913 A | 10/1999 | Newkirk | |
| 6,128,522 A | 10/2000 | Acker et al. | |
| 6,155,970 A | 12/2000 | Dykes | |
| 6,157,278 A | 12/2000 | Katznelson et al. | |
| 6,208,142 B1 | 3/2001 | Wagshul | |
| 6,228,106 B1 | 5/2001 | Simbruner | |
| 6,231,499 B1 | 5/2001 | Jones | |
| D446,675 S | 8/2001 | Straub | |
| 6,278,274 B1 | 8/2001 | Biglieri et al. | |
| 6,317,618 B1 | 11/2001 | Livni | |
| 6,323,647 B1 | 11/2001 | Anderson et al. | |
| 6,409,654 B1 | 6/2002 | McClain | |
| 6,433,548 B1 | 8/2002 | Furuta | |
| 6,471,634 B1 | 10/2002 | Dykes | |
| 6,502,042 B1 | 12/2002 | Eid et al. | |
| 6,511,414 B1 | 1/2003 | Hamsund | |
| 6,611,702 B2 | 8/2003 | Rohling et al. | |
| 6,641,521 B2 | 11/2003 | Kolarovic | |
| 6,666,816 B2 | 12/2003 | Mountain | |
| RE38,453 E | 3/2004 | Lessard | |
| 6,776,527 B1 | 8/2004 | Tybinkowski | |
| 6,860,272 B2 | 3/2005 | Carter | |
| 6,992,486 B2 | 1/2006 | Srinivasan | |
| 7,071,692 B2 | 7/2006 | Branch et al. | |
| 7,255,671 B2 | 8/2007 | Boone | |
| 7,274,192 B2 | 9/2007 | Havens | |
| 7,278,962 B2 | 10/2007 | Lonneker-Lammers | |
| D567,948 S | 4/2008 | Tierney | |
| 7,378,848 B2 | 5/2008 | Gao et al. | |
| 7,399,220 B2 | 7/2008 | Krisel et al. | |
| 7,482,558 B2 | 1/2009 | Koch | |
| 7,486,982 B2 | 2/2009 | Branch et al. | |
| 7,599,728 B2 | 10/2009 | Feenan | |
| 7,614,692 B2 | 11/2009 | Biaud | |
| 7,621,815 B2 | 11/2009 | Bosserdet, Jr. | |
| 7,760,084 B2 | 7/2010 | Jensen et al. | |
| 7,777,491 B2 | 8/2010 | Gao et al. | |
| 7,784,121 B2 | 8/2010 | Ahlman | |
| 8,087,203 B2 | 1/2012 | Boesel et al. | |
| 8,118,488 B2 | 2/2012 | Gregerson | |
| 8,147,396 B2 | 4/2012 | Srinivasan | |
| 8,375,295 B2 | 2/2013 | Zalewski et al. | |
| 8,525,116 B2 | 9/2013 | Schulz et al. | |
| 8,555,578 B2 | 10/2013 | Hushek | |
| 8,583,294 B2 | 11/2013 | Villano et al. | |
| 8,807,084 B2 | 8/2014 | Rapoport et al. | |
| 8,851,018 B2 | 10/2014 | Rapoport et al. | |
| 8,896,310 B2 | 11/2014 | Rapoport | |
| 8,924,848 B2 | 12/2014 | Klinger | |
| 8,924,869 B2 | 12/2014 | Fellman | |
| 8,930,831 B2 | 1/2015 | Bartomeli et al. | |
| 8,984,426 B2 | 3/2015 | Endoh et al. | |
| 9,003,318 B2 | 4/2015 | Magnusson et al. | |
| 9,055,912 B2 | 6/2015 | Graumann et al. | |
| 9,597,246 B2 | 3/2017 | Rapoport | |
| 9,599,683 B2 | 3/2017 | Armstrong et al. | |
| 9,974,705 B2 | 5/2018 | Rapoport | |
| 2001/0038489 A1 | 11/2001 | Nakamura et al. | |
| 2001/0049465 A1 | 12/2001 | Goldberg | |
| 2002/0072648 A1 | 6/2002 | Dykes | |
| 2002/0123681 A1 | 9/2002 | Zuk et al. | |
| 2002/0143233 A1 | 10/2002 | Donnelly | |
| 2002/0173717 A1* | 11/2002 | Rohling ............... | A61B 5/0555 600/415 |
| 2003/0016518 A1 | 1/2003 | Arz | |
| 2003/0088175 A1 | 5/2003 | Branch et al. | |
| 2004/0030241 A1 | 2/2004 | Green | |
| 2004/0034273 A1 | 2/2004 | Boris | |
| 2004/0106844 A1 | 6/2004 | Lonneker-Lammers | |
| 2004/0116799 A1* | 6/2004 | Srinivasan ........... | A61B 5/0555 600/410 |
| 2004/0127786 A1* | 7/2004 | Schmit ................. | A61B 6/0442 600/422 |
| 2004/0133064 A1 | 7/2004 | Castillon Levano | |
| 2004/0135687 A1 | 7/2004 | Keene | |
| 2004/0147833 A1 | 7/2004 | Czipott et al. | |
| 2004/0186341 A1 | 9/2004 | McDermott | |
| 2004/0190643 A1 | 10/2004 | Branch et al. | |
| 2004/0194989 A1 | 10/2004 | Branch et al. | |
| 2004/0196043 A1 | 10/2004 | Branch | |
| 2005/0020906 A1 | 1/2005 | Seijger | |
| 2005/0027189 A1 | 2/2005 | Branch et al. | |
| 2005/0038314 A1 | 2/2005 | Falk | |
| 2005/0113668 A1 | 5/2005 | Srinivasan | |
| 2005/0242817 A1 | 11/2005 | Hoult | |
| 2006/0022670 A1 | 2/2006 | Kumar et al. | |
| 2006/0084857 A1 | 4/2006 | Massengill et al. | |
| 2006/0247487 A1 | 11/2006 | Arts | |
| 2006/0267585 A1 | 11/2006 | Havens | |
| 2007/0056593 A1 | 3/2007 | Kubicsko | |
| 2007/0135704 A1 | 6/2007 | Branch et al. | |
| 2007/0203481 A1 | 8/2007 | Gregg et al. | |
| 2007/0232894 A1* | 10/2007 | Feenan ................. | A61B 5/055 600/410 |
| 2007/0238950 A1 | 10/2007 | Vija et al. | |
| 2008/0021317 A1 | 1/2008 | Sumanaweera | |
| 2008/0103388 A1 | 5/2008 | Maschke et al. | |
| 2008/0122441 A1 | 5/2008 | Hayakawa | |
| 2008/0171931 A1 | 6/2008 | Maschke | |

(56) References Cited

U.S. PATENT DOCUMENTS

| | | |
|---|---|---|
| 2008/0163425 A1 | 7/2008 | White |
| 2008/0204028 A1 | 8/2008 | DeVries et al. |
| 2008/0234571 A1 | 9/2008 | Hay et al. |
| 2008/0281187 A1 | 11/2008 | Massengill et al. |
| 2009/0209846 A1 | 8/2009 | Bammer |
| 2009/0213997 A1 | 8/2009 | Maschke |
| 2010/0004502 A1 | 1/2010 | Honma |
| 2010/0066368 A1 | 3/2010 | Gao et al. |
| 2010/0145358 A1 | 6/2010 | Maschke |
| 2010/0154325 A1* | 6/2010 | Boesel ............... H05K 9/0018 52/173.1 |
| 2010/0168502 A1 | 7/2010 | Delaporte |
| 2010/0219347 A1 | 9/2010 | Schulz et al. |
| 2010/0245543 A1 | 9/2010 | Greer et al. |
| 2011/0048424 A1 | 3/2011 | Radko |
| 2011/0113555 A1 | 5/2011 | Smith |
| 2011/0125010 A1 | 5/2011 | Vaquero Lopez |
| 2011/0162652 A1 | 7/2011 | Rapoport |
| 2011/0186049 A1 | 8/2011 | Rapoport |
| 2011/0234347 A1 | 9/2011 | Rapoport |
| 2011/0274238 A1 | 11/2011 | Maschke |
| 2011/0280364 A1 | 11/2011 | Maschke |
| 2011/0280380 A1 | 11/2011 | Maschke |
| 2011/0282184 A1 | 11/2011 | Klingenbeck et al. |
| 2011/0304333 A1 | 12/2011 | Rapoport |
| 2012/0071745 A1 | 3/2012 | Rapoport |
| 2012/0073511 A1 | 3/2012 | Rapoport et al. |
| 2012/0077707 A1 | 3/2012 | Rapoport |
| 2012/0078034 A1 | 3/2012 | Falk |
| 2012/0119742 A1 | 5/2012 | Rapoport |
| 2012/0126814 A1 | 5/2012 | Fischer et al. |
| 2013/0079624 A1 | 3/2013 | Rapoport |
| 2013/0109956 A1 | 5/2013 | Rapoport |
| 2013/0150656 A1* | 6/2013 | Falk ..................... A61B 5/0555 600/22 |
| 2013/0204074 A1 | 8/2013 | Belval |
| 2013/0204617 A1 | 8/2013 | Kuo |
| 2013/0237803 A1 | 9/2013 | Rapoport |
| 2013/0267765 A1 | 10/2013 | Rapoport |
| 2013/0328559 A1 | 12/2013 | Rapoport |
| 2013/0328560 A1 | 12/2013 | Rapoport |
| 2013/0328563 A1 | 12/2013 | Rapoport |
| 2014/0003614 A1 | 1/2014 | Levitov |
| 2014/0050827 A1 | 2/2014 | Rapoport |
| 2014/0051973 A1 | 2/2014 | Rapoport et al. |
| 2014/0051974 A1 | 2/2014 | Rapoport et al. |
| 2014/0051976 A1 | 2/2014 | Rapoport et al. |
| 2014/0078301 A1 | 3/2014 | Fazzi |
| 2014/0099010 A1 | 4/2014 | Rapoport |
| 2014/0103927 A1 | 4/2014 | Rapoport |
| 2014/0117989 A1 | 5/2014 | Rapoport |
| 2014/0128725 A1 | 5/2014 | Rapoport |
| 2014/0139216 A1 | 5/2014 | Rapoport |
| 2014/0142914 A1 | 5/2014 | Rapoport |
| 2014/0152302 A1 | 6/2014 | Rapoport et al. |
| 2014/0152310 A1 | 6/2014 | Rapoport |
| 2014/0158062 A1 | 6/2014 | Rapoport et al. |
| 2014/0230850 A1 | 8/2014 | Rapoport |
| 2014/0257081 A1 | 9/2014 | Rapoport |
| 2014/0266203 A1 | 9/2014 | Rapoport |
| 2014/0300358 A1 | 10/2014 | Rapoport |
| 2014/0354279 A1 | 12/2014 | Dumoulin et al. |
| 2014/0354282 A1 | 12/2014 | Kusik et al. |
| 2014/0357981 A1 | 12/2014 | Dumoulin |
| 2014/0364722 A1 | 12/2014 | Dumoulin |
| 2014/0378821 A1 | 12/2014 | Rapoport et al. |
| 2014/0378825 A1 | 12/2014 | Rapoport et al. |
| 2015/0005618 A1 | 1/2015 | Dumoulin |
| 2015/0059157 A1 | 3/2015 | Rapoport |
| 2015/0059655 A1 | 3/2015 | Rapoport |
| 2015/0065788 A1 | 3/2015 | Rapoport |
| 2015/0077105 A1 | 3/2015 | Rapoport et al. |
| 2015/0137812 A1 | 5/2015 | Rapoport |
| 2015/0141799 A1 | 5/2015 | Rapoport et al. |
| 2015/0226817 A1 | 8/2015 | Pourrahimi |
| 2015/0230766 A1 | 8/2015 | Wang et al. |
| 2016/0030264 A1 | 2/2016 | Lehmann |
| 2016/0081582 A1 | 3/2016 | Rapoport |
| 2016/0089054 A1* | 3/2016 | Rapoport ............... G01R 33/30 600/415 |
| 2017/0143271 A1 | 5/2017 | Gustafsson et al. |
| 2017/0146619 A1 | 5/2017 | Strauss et al. |
| 2017/0181912 A1 | 6/2017 | Rapoport et al. |

FOREIGN PATENT DOCUMENTS

| | | |
|---|---|---|
| CN | 101185383 | 5/2008 |
| CN | 201846566 | 5/2011 |
| CN | 102551719 A | 7/2012 |
| DE | 19617739 | 6/1997 |
| DE | 102008009673 | 8/2009 |
| DE | 102008009674 | 8/2009 |
| DE | 102011109375 | 2/2013 |
| DE | 202013104656 | 10/2013 |
| EP | 0187691 | 7/1986 |
| EP | 2581071 | 4/2013 |
| EP | 2607977 | 6/2013 |
| IL | 226488 | 5/2013 |
| JP | S5961763 | 9/1984 |
| JP | 04317630 | 11/1992 |
| JP | 2004531313 | 10/2004 |
| JP | 2007-252741 | 10/2007 |
| JP | 2010178857 | 8/2010 |
| WO | WO1998048756 | 11/1998 |
| WO | 9921526 | 5/1999 |
| WO | WO2004029644 | 4/2004 |
| WO | 2011109761 | 9/2011 |
| WO | WO2012004797 | 1/2012 |
| WO | 2012143825 A1 | 10/2012 |
| WO | WO2013115847 | 8/2013 |

OTHER PUBLICATIONS

International Standard, CEI IEC 60601-1-8, Second Edition, Oct. 2006, Medical electrical equipment, Part 1-8:1-166.

SASO IEC 60601-1-10, Medical electrical equipment, Part 1-10: General requirements for basic safety and essential performance, Collateral Standard: Requirements for the development of physiologic closed-loop controllers, 2008, 1-36.

International Standard, CEI IEC 60601-1, Third Edition, Dec. 2005, Medical electrical equipment, Part 1, 1-393.

International Standard, CEI IEC 60601-2-19, Edition 2.0, Feb. 2009, Medical electrical equipment—Part 2-19: Particular requirements for the basic safety and essential performance of infant incubators, 1-80.

Advanced Healthcare Technology, "Baby Pod II: Infant Transport Device", pp. 1-6, accessed online on May 26, 2016.

Advanced Heathcare Technology, "Baby Pod II: Operating & Maintenance Manual", revised Jan. 2011, pp. 1-14.

Aspect Imaging Ltd. "MRI RF Shielding Jacket", co-pending U.S. Appl. No. 14/623,051, filed Feb. 16, 2015.

Aspect Imaging Ltd. "MRI Thermo-Isolating Jacket", co-pending U.S. Appl. No. 14/623,039, filed Feb. 16, 2015.

Aspect Imaging Ltd., "Foamed Patient Transport Incubator", co-pending U.S. Appl. No. 14/531,289, filed Nov. 3, 2014.

Aspect Imaging Ltd., "Incubator Deployable Multi-Functional Panel", co-pending U.S. Appl. No. 14/619,557, filed Feb. 11, 2015.

Aspect Imaging Ltd., "Incubator's Canopy with Sensor Dependent Variably Transparent Walls and Methods for Dimming Lights Thereof", co-pending U.S. Appl. No. 14/453,909, filed Aug. 7, 2014.

Aspect Imaging Ltd., "Means and Method for Operating an MRI Device Within a RF-Magnetic Environment", copending U.S. Appl. No. 14/596,329, filed Jan. 14, 2015.

Aspect Imaging Ltd., "Means for Operating an MRI Device Within a RF-Magnetic Environment", co-pending U.S. Appl. No. 14/596,320, filed Jan. 14, 2015.

Aspect Imaging Ltd., "Mechanical Clutch for MRI", co-pending U.S. Appl. No. 14/611,379, filed Feb. 2, 2015.

(56) References Cited

OTHER PUBLICATIONS

Aspect Imaging Ltd., "Shutting Assembly for Closing an Entrance of an MRI Device", co-pending U.S. Appl. No. 14/540,163, filed Nov. 13, 2014.

International Search Report of PCT Application No. PCT/IL2014/050987, dated Mar. 16, 2015. 3 pages.

Israeli Office Action (with English language translation) for Application No. IL245643, dated Dec. 8, 2019, 6 pages.

Jenkins, S., ScanPod, Baby Pod-Products-Scan Pod, 2002-2011 Advance Healthcare Technology, ltd., internet website http://babypod.com:80/products/scanpod.php, 1 page.

Notice of Allowance dated Feb. 26, 2020 for U.S. Appl. No. 15/424,428 (pp. 1-8).

Paley et al., An MR-compatible neonatal incubator, The British Journal of Radiology, 85, 2012, 952-958.

Rapoport, Uri, "RF Shielding Conduit in an MRI Closure Assembly", co-pending U.S. Appl. No. 14/574,785, filed Dec. 18, 2014.

Science Daily, Inside the preemie brain, Incubator enables MRI scans on premeeies for preventing birth asphyxia, Dec. 1, 2005, pp. 1-2, Web address: http://web.archive.org/web/20130303154220/http://www.sciencedaily.com/videos/200 5/1211-inside_the_preemie_brain.htm.

\* cited by examiner

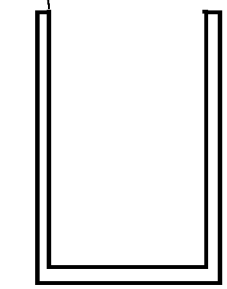
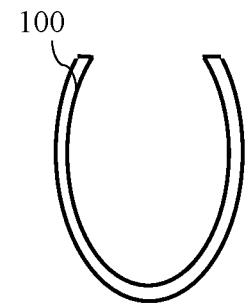
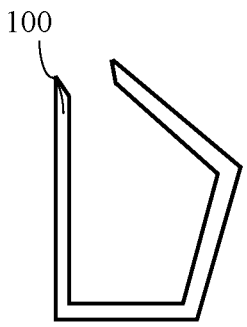
Fig. 1A　　Fig. 1B　　Fig. 1C
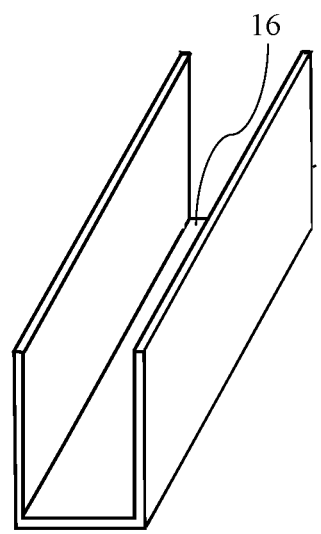
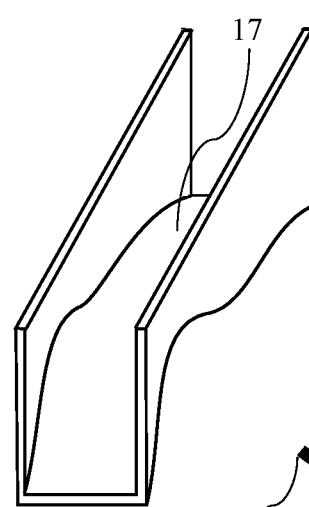
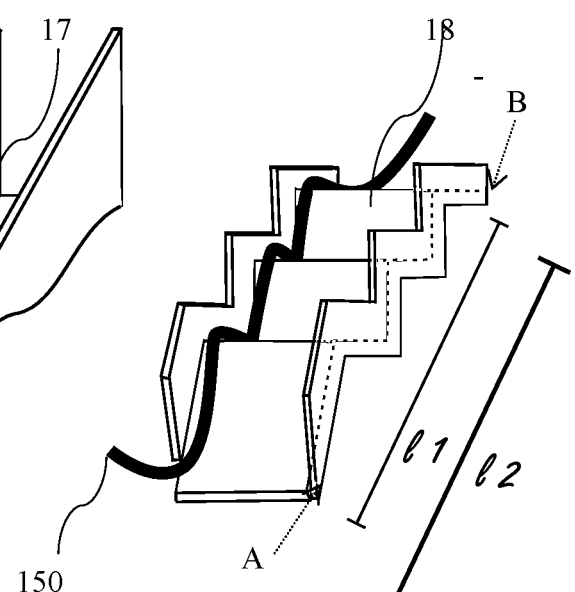
Fig. 1D　　Fig. 1E　　Fig. 1F

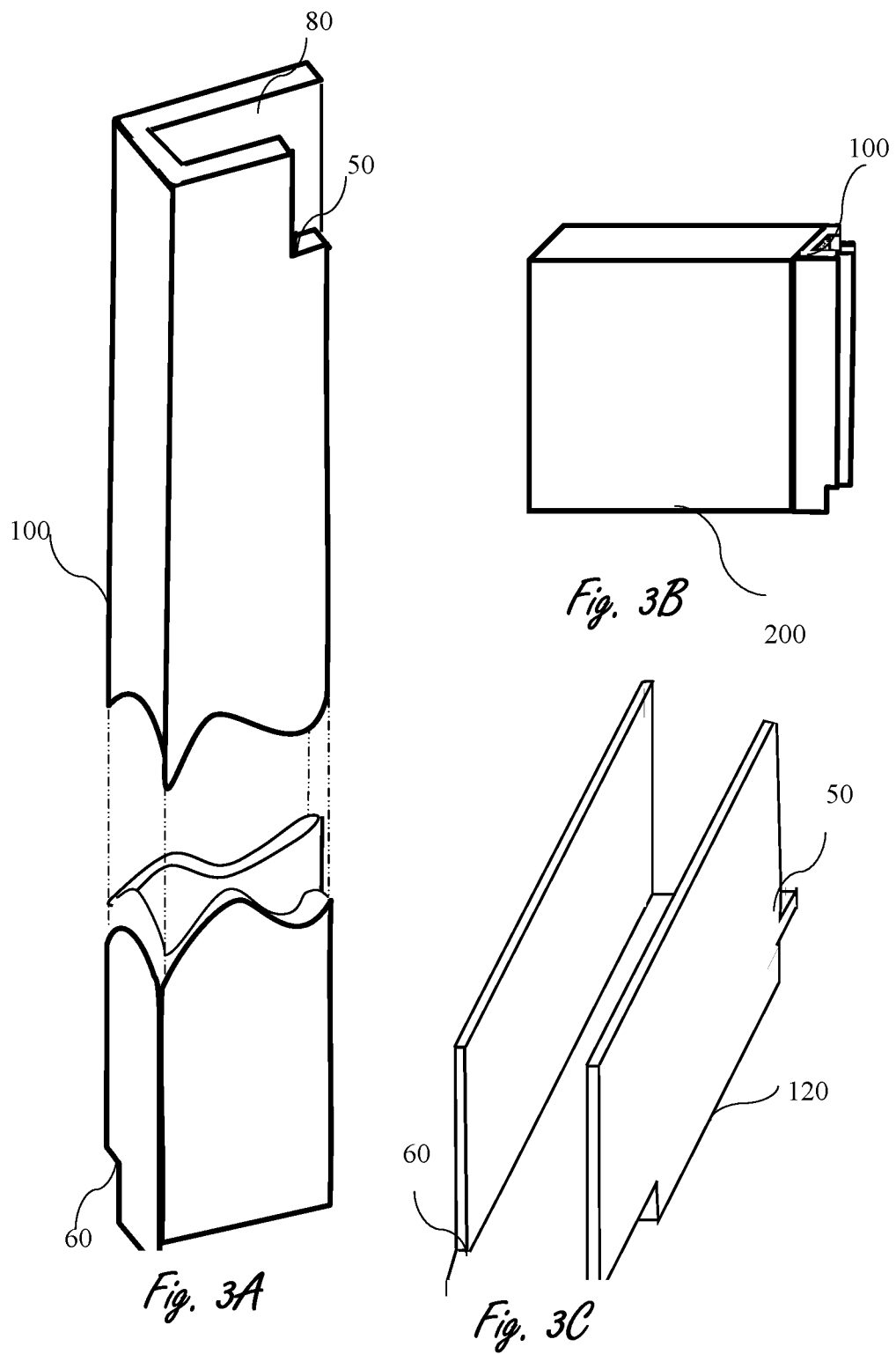

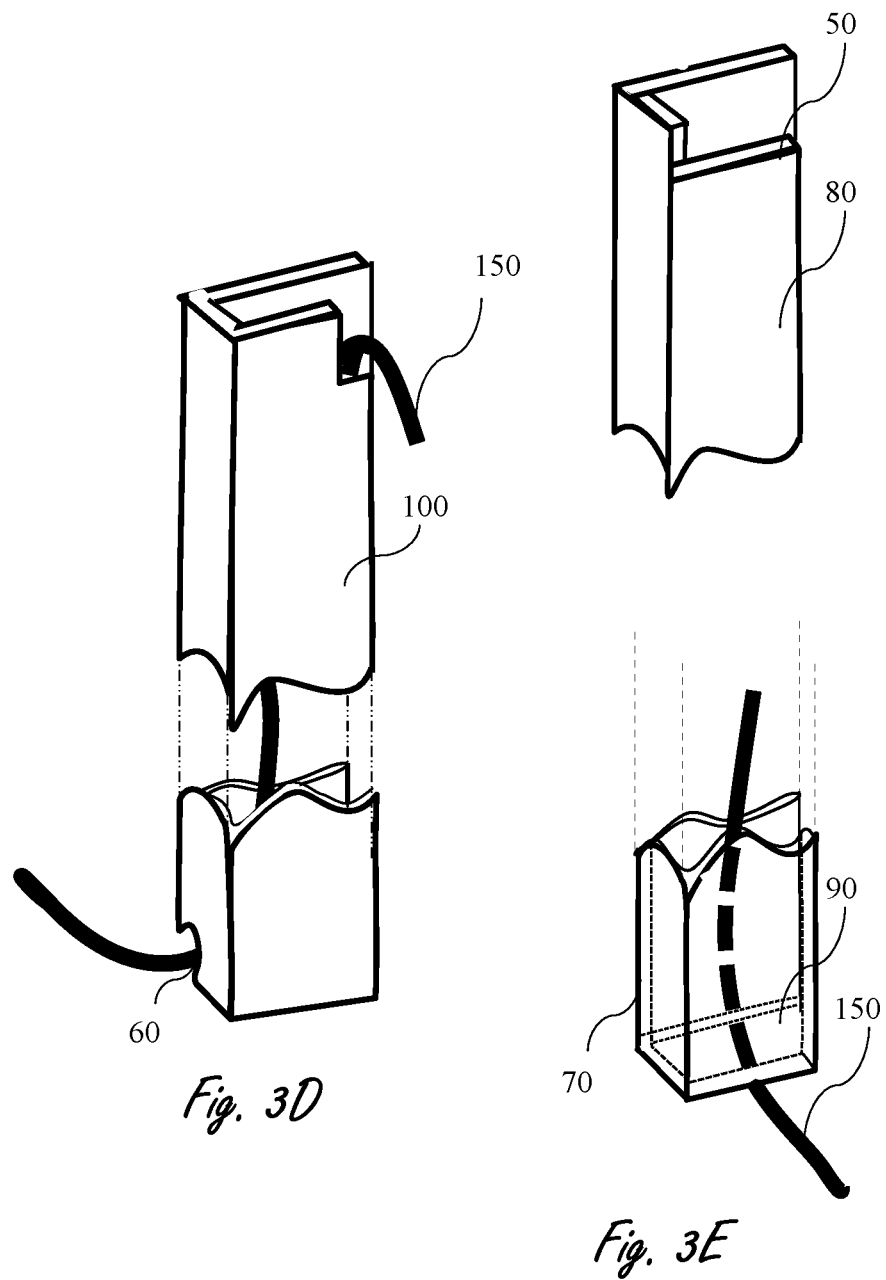

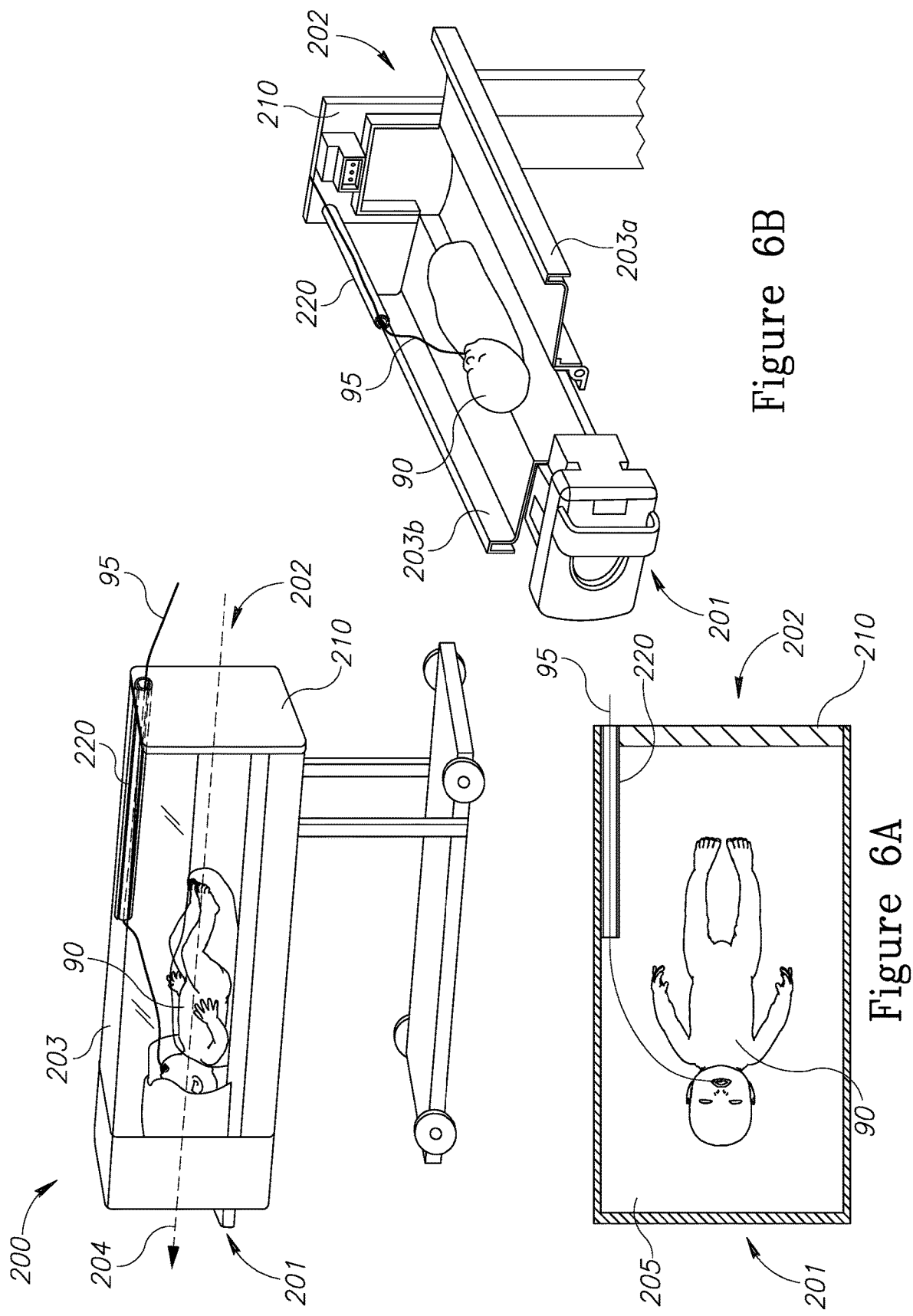

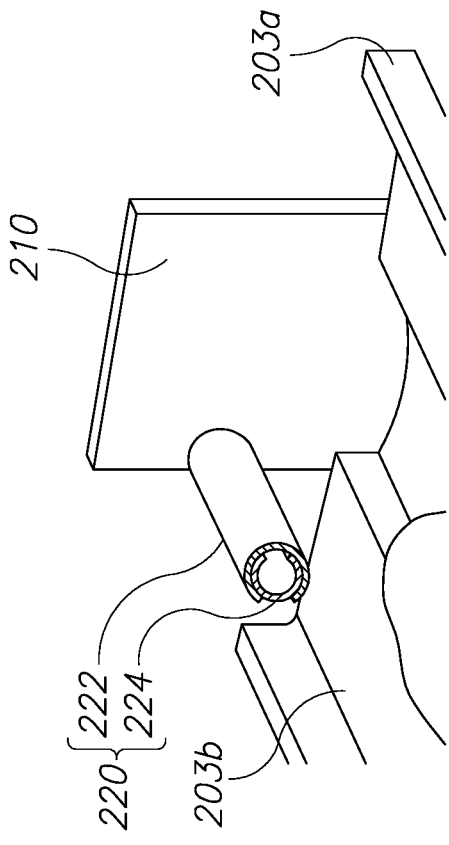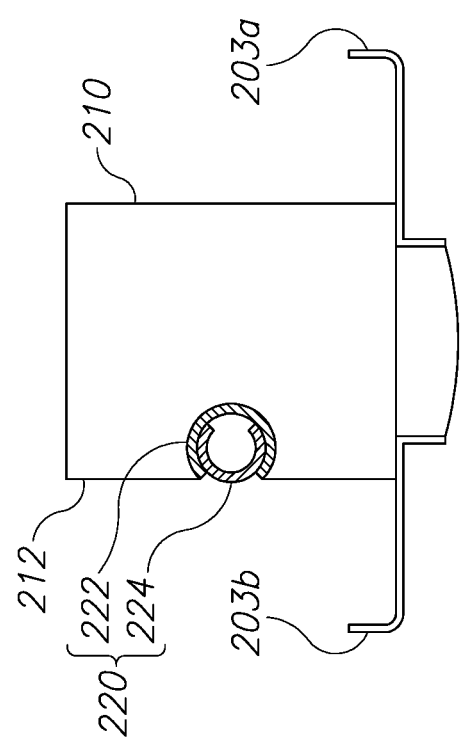
Figure 7B

RF SHIELDING CHANNEL IN MRI-INCUBATOR'S CLOSURE ASSEMBLY

CROSS REFERENCE TO RELATED APPLICATIONS

This application is a continuation-in-part of U.S. patent application Ser. No. 14/539,442, filed on Nov. 12, 2014, which claims priority to U.S. Provisional Application No. 61/905,221, filed on Nov. 17, 2013, all of which are incorporated herein by reference in their entireties. This application is also a continuation-in-part of U.S. patent application Ser. No. 15/424,428, filed on Feb. 3, 2017, which is a continuation of U.S. patent application Ser. No. 13/233,515, filed on Sep. 15, 2011, which claims priority to U.S. Provisional Application No. 61/383,349, filed on Sep. 16, 2010, all of which are incorporated herein by reference in their entireties.

FIELD OF THE INVENTION

The present invention generally relates to the field of magnetic resonance imaging systems (MRI), and more particularly, to an incubator closure assembly intended to hermetically shut an entrance of an MRI bore comprising passage for medical equipment that maintains RF waveguide attenuation shielding during its operation and methods thereof.

BACKGROUND OF THE INVENTION

MRI technology utilizes magnetism and radio frequency for imaging of patients for medical diagnosis and research. Electromagnetic interference (EMI) that is generated in the process of MRI negatively affects other devices in its vicinity such as medical electrical devices, computers, data transfer components, other scanning devices, etc. In addition EMI generated at an external source such as electric lines, television and radio signals, elevators, etc., can impede MRI operation and results.

Facilities providing MRI services build specially designed rooms that allow MRI procedures to be shielded from these interferences, while preventing leakage of the same interferences to the outside.

This shielding may include passive or active components to achieve magnetic and RF shielding. For example, to achieve RF shielding, the walls, floor and ceiling are built from sheets of conductive metal such as copper, aluminum, etc., including a door that maintains a closed circuit with the walls. Magnetic shielding could be provided by constructing a magnetic shield around the RF shield. A passive solution involves using magnetic shielding material, typically metal or metal alloy. These materials would need to be comprised of a very high permeability material such as "mu-metal". The second option would be an active magnetic cancellation system, that would typically include a magnetometer, controller, amplifier and compensation coils. This solution tends to be costly and requires adjusting and handling.

In order to provide a passage for systems such as air conditioning, electrical wiring, communication devices, medical equipment, etc., into EMI shielded rooms, means such as waveguide attenuators and RF filters are used. All fluid and air passing tubes are threaded through a conduit that is configured to attenuate EMI, and all electrical or conductive wiring is connected through an RF filter to avoid coupling of RF to the conductive wire. These means require pre-planning, and pre-insertion of each tube and cable to a previously constructed designated location. In addition, in order to thread cables and tubes though these devices they need to be disconnected from at least one side.

Many patients are in need of medical support or monitoring during MRI. These include neonates, sedated patients, or other medically unstable patients. It is of critical importance to maintain life support and monitoring conditions of these patients also when undergoing MRI. Disconnecting medical equipment for the purpose of threading it into their designated positions takes time and may cause patient stress, or induce medical complications. Emergency situations requiring the quick extraction of the patient are also hindered by the need to detach medical equipment from the MRD. In addition the number of cables and tubes are limited to the pre-built passages in the room.

An MRI scanner utilizes a very strong magnet, thus iron-containing objects positioned in the vicinity of an MRI machine are pulled into an MRI bore. Numerous severe accidents were recorded at MRI facilities because of pulled iron-containing objects. Keeping the MRD bore open for the passage of medical equipment may leave a space through which projectile objects could enter.

There is a long felt need for an apparatus that will provide physical, EMI, and RF shielding, while allowing passage for medical and life supporting equipment without compromising this shielding. Further there is need for a passage that allows the patient's MRI procedure to take place without disconnecting the medical and monitoring equipment from him. In addition, there is a need for an apparatus that enables quick release of the patient from the MRD in case of immediate need.

SUMMARY OF THE INVENTION

The present invention provides a magnetic resonance imaging device (MRD) having an open bore extended along the MRD's longitudinal axis with a distal end and proximal end, the bore is terminated by an aperture located in the proximal end, into which a neonate's incubator is inserted, an incubator's closure assembly adapted to hermetically shut the aperture when the incubator is accommodated within the open bore, the closure assembly comprising at least one U-shaped conduit having (i) an array of distal and proximal sealing walls, both are substantially perpendicular to the longitudinal axis and having upwards and downwards directions, and (ii) a recess in between the walls having length, having upwards to downwards direction, and width, having distal to proximal direction, each of the proximal wall and the distal wall comprising a cutout at opposite directions, and wherein in the recess, the ratio of length to width is greater than a predefined value n.

It is another object of the current invention to disclose the incubator's closure assembly as described above, wherein the conduit is connected in a non-protruding manner to an incubator's closure assembly, thereby, no direct access is provided between the MRD bore and the external environment.

It is another object of the current invention to disclose the incubator's closure assembly as described above, wherein the conduit cutouts are adapted by means of size and shape to permit passage of medical equipment within, from the inner space of the MRD bore to the external environment.

It is another object of the current invention to disclose the incubator's closure assembly as described above, wherein the conduit wall along the longitudinal axis is of a shape selected from a group consisting of: straight, curved, polygonal, symmetrical, non-symmetrical and any combination thereof.

It is another object of the current invention to disclose the incubator's closure assembly as described above, wherein the conduit open face is adapted by size and shape to enable removal of at least a portion of medical equipment passing within the conduit, without detaching it from any of the equipment ends.

It is another object of the current invention to disclose the incubator's closure assembly as described above, wherein at least a portion of the conduit cutouts comprising a curved profile edge.

It is another object of the current invention to disclose the incubator's closure assembly as described above, wherein at least a portion of the conduit walls edge profiles are of a smoothed finish.

It is another object of the current invention to disclose the incubator's closure assembly as described above, wherein at least a portion of the conduit is perforated; further wherein the perforations are of a length and diameter configured as a waveguide RF attenuator, thereby allowing for RF shielding together with light and air penetration into the MRD.

It is another object of the current invention to disclose the incubator's closure assembly as described above, wherein the conduit is constructed as a reversibly detachable module.

It is another object of the current invention to disclose the incubator's closure assembly as described above, wherein the conduit is connected to the incubator's closure assembly at a location comprising at least a portion of the border between the closure assembly and the aperture in the MRD bore proximal end.

It is another object of the current invention to disclose the incubator's closure assembly as described above, wherein the conduit location enables removal of at least a portion of medical equipment passing within the conduit when the assembly is retracted from the MRD bore, without detaching the equipment from any of the equipment ends.

It is another object of the current invention to disclose the incubator's closure assembly as described above, wherein the conduit further comprises an RF filter, configured to permit electrical wiring to pass into the MRD bore from the external environment.

It is another object of the current invention to disclose the incubator's closure assembly as described above, wherein at least a portion of the conduit comprising shielding selected from a group consisting of: magnetic shielding, RF shielding, physical shielding and any combination thereof.

It is another object of the current invention to disclose the incubator's closure assembly as described above, wherein the conduit further comprising at least a portion of transparent material.

It is another object of the current invention to disclose the incubator's closure assembly as described above, wherein the conduit is configured by means of size, shape and material to attenuate the passage of radio frequencies at a range of the values of X to Y MHz; further wherein the values of X and Y are selected from a group consisting of: X>0 MHz and Y<1000 MHz, X>0 MHz and Y<500 MHz, X>0 MHz and Y<200 MHz and any combination thereof.

It is another object of the current invention to disclose the incubator's closure assembly as described above, wherein at least one of the walls is maneuverably connected to the longitudinal wall remaining in a fixed position.

It is another object of the current invention to disclose the incubator's closure assembly as described above, wherein the assembly is adapted by means of size and shape to be connected to an MRI-compatible cart in connection with an MRI-compatible neonate's cradle.

The present invention provides a method for RF shielding an MRD from its external environment generated EMI, and RF shielding the external environment from the MRD generated EMI, by providing an RF shielding conduit, the method comprising steps of: (a) obtaining an MRD, and an incubator connected to an incubator's closure assembly comprising at least one U-shaped RF shielding conduit, the conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and in the recess, the ratio of length to width is greater than a predefined value n; (b) inserting the incubator containing patient into the MRD bore, thereby shutting MRD bore with incubator closure assembly; (c) imaging patient; opening the MRI bore by extracting the incubator; and (d) extracting patient, wherein the conduit is connected in a non-protruding manner to an incubator's closure assembly, thereby, no direct access is provided between the MRD bore and the external environment.

The present invention provides a method for manufacturing an incubator's closure assembly comprising a U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), comprising the steps of: (a) obtaining an incubator closure assembly; (b) defining dimensions of a U-shaped conduit to fit passage of medical equipment within; (c) defining the recess, so that the ratio of length to width is than a predefined value n; (d) forming the conduit; (e) forming cutouts at opposite directions in the distal and proximal walls of the conduit; and (f) connecting the conduit to incubator's closure assembly so the open longitudinal face is open towards the external environment, wherein the conduit is connected in a non-protruding manner to an incubator's closure assembly, thereby, no direct access is provided between the MRD bore and the external environment.

The present invention provides a standard of care protocol for magnetic resonance imaging a patient placed within an incubator, connected to medical equipment, whilst not leaking RF into the MRD and from the MRD, further enabling a one-step insertion or exertion of patient from MRD without detaching connected medical equipment, characterized by providing an incubator's closure assembly adapted to hermetically shut a magnetic resonance imaging device (MRD) having an open bore extended along the MRD's longitudinal axis with a distal end and proximal end, the bore is terminated by an aperture located in the proximal end, into which a neonate's incubator is inserted, when the incubator is accommodated within the open bore, the closure assembly comprising a U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and in the recess, the ratio of length to width is greater than a predefined value n, wherein at least one of the following is held true: (a) the average number of patient's health complications due to multi-step extraction of patients from MRD in an emergency is z times higher than when utilizing the incubator's closure assembly, z is equal or greater than 1.05; (b) the average number of MRD associated patient's health complications due to detaching and attaching medical equipment to the patient is i times higher than when utilizing the incubator's closure assembly i is equal or greater than 1.05; (c) the average number of insurable claims of a selected from a group consisting of: manufacturer, handler, user, operator, medical care personal, medical facility, medical facility management or any combination thereof when utilizing the incubator's closure assembly is m times lower than patient MRI associated insurable claims; m is equal or greater than 1.05; (d) the average number of repeated MRI due to EMI created artifacts when utilizing the incubator's closure assembly is p times lower than the average number of repeated MRI; p is equal or greater than 1.05; (e) the average number of reported incidents of EMI interfering with medical equipment during MRI when utilizing the incubator's closure assembly is 5 times lower than the average number of reported incidents of EMI interfering with medical equipment during MRI; 5 is equal or greater than 1.05; (f) the average stress levels of patients measured by the average levels of the patient salival cortisol during MRI when utilizing the incubator's closure assembly is t times lower than the average stress levels of patients during MRI; t is equal or greater than 1.05; (g) the average number of patient's health complications due to artifacts in MRD images caused by EMI is r times higher than when utilizing the incubator's closure assembly; r is equal or greater than 1.05; (h) the average number of patient's health complications due EMI interfering with medical equipment is u times higher than when utilizing the incubator's closure assembly; u is equal or greater than 1.05; and (i) the average number of EMI incidents of interfering with imaging equipment is w times higher than when utilizing the incubator's closure assembly; w is equal or greater than 1.05.

One aspect of the present invention provides a neonate incubator for positioning a neonate within a magnetic resonance imaging (MRI) device, the neonate incubator including: a proximal end and a distal end; a radio frequency (RF) shielding door coupled to the distal end, the RF shielding door to mate with a bore of the MRI device to provide RF shielding; and a RF channel that extends along an axis that is substantially parallel to a longitudinal axis of the neonate incubator from an interior chamber of the neonate incubator through the RF shielding door, the RF channel having a length to width ratio of at least 5 to 1.

In some embodiments, the RF channel to enable a passage of a tubing of medical equipment from the interior chamber of the neonate incubator to an environment that is external to the neonate incubator.

In some embodiments, the RF channel including: a first cylindrical shell having a first cutout in a longitudinal direction along the shell, the first cutout is positioned adjacent to an outer edge of the RF shielding door; and a second cylindrical shell positioned coaxially within the first cylindrical shell, the second cylindrical shell having a second cutout in a longitudinal direction along the shell and a substantially hollow interior, the second cylindrical shell is rotatable around a longitudinal axis of the shell.

In some embodiments, the second cutout of the second cylindrical shell to be aligned with the first cutout of the first cylindrical shell to enable an insertion of the tubing of medical equipment within the substantially hollow interior of the second cylindrical shell via the first and the second cutouts.

In some embodiments, the RF channel to enclose the tubing of medical equipment upon shifting of the second cutout of the second cylindrical shell to a position that is substantially opposite with respect to the first cutout of the first cylindrical shell.

In some embodiments, the RF shieling includes preventing an external RF radiation from entering the bore of the MRI device and an RF radiation emitted by the MRI device from exiting the bore of the MRI device.

In some embodiments, at least a portion of the RF channel is positioned within the interior chamber of the incubator.

In some embodiments, the RF channel to enable an insertion of the tubing of medical equipment without detaching the tubing from any of the medical equipment ends.

In some embodiments, the RF channel further includes at least one holder to hold a position of the tubing of medical equipment passing through the RF channel.

In some embodiments, further includes at least one holder connected to the RF shielding door to hold a position of the tubing of medical equipment.

In some embodiments, the at least one holder includes: a first flexible element having a first proximal end and a first distal end, the first flexible element is connected to the RF shielding door at the first proximal end; a second flexible element having a second proximal end and a second distal end, the second flexible element is connected to the RF shielding door at the second proximal end; and a gap bounded by the first flexible element, the second flexible element and a portion of the RF shielding door between the first and second proximal ends.

In some embodiments, at least a portion of the first distal of the first flexible element end overlaps with at least a portion of the second distal end of the second flexible element forming thereby a first overlapping portion and a second overlapping portion.

In some embodiments, the first overlapping portion is closer to the RF shielding door than the second overlapping portion.

In some embodiments, the second overlapping portion is closer to the RF shielding door than the first overlapping portion.

In some embodiments, the tubing of medical equipment is positioned within the gap by pushing the tubing of medical equipment against the first distal end of the first flexible element and wherein the tubing of medical equipment is released from the gap by pushing the tubing of medical equipment against the second distal end of the second flexible element.

In some embodiments, the tubing of medical equipment is positioned within the gap by pushing the tubing of medical equipment against the second distal end of the second flexible element and wherein the tubing of medical equipment is released from the gap by pushing the tubing of medical equipment against the first distal end of the first flexible element.

In some embodiments, the first and second flexible elements having a substantially L-shape.

BRIEF DESCRIPTION OF THE DRAWINGS

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. In the accompanying drawing:

FIG. 1A is a schematic illustration of an embodiment of the U shaped conduit, in a side view profile;

FIG. 1B is a schematic illustration of an embodiment of the U shaped conduit, in a side view profile;

FIG. 1C is a schematic illustration of an embodiment of the U shaped conduit, in a side view profile;

FIG. 1D is a schematic illustration of an embodiment of the U shaped conduit, in a perspective view, illustrating an embodiment of the longitudinal axis wall;

FIG. 1E is a schematic illustration of an embodiment of the U shaped conduit, in a perspective view, illustrating an embodiment of the longitudinal axis wall;

FIG. 1F is a schematic illustration of an embodiment of the U shaped conduit, in a perspective view, illustrating an embodiment of the longitudinal axis wall;

FIG. 3A is a schematic illustration of an embodiment of a conduit in a perspective view (100);

FIG. 3B is a schematic illustration of an embodiment of the arrangement of a conduit along the side contour of a rectangular embodiment of a closure assembly;

FIG. 3C is a schematic illustration of an embodiment of a conduit fit to connect as a detachable module;

FIG. 3D is a schematic illustration of an embodiment of a conduit cut outs, and the arrangement of a tube passing through them;

FIG. 3E is a schematic illustration of an embodiment of the conduit cutouts and arrangement of a tube passing through the conduit bottom opening;

FIGS. 6A-6B are illustrations of a neonate incubator for positioning a neonate within a magnetic resonance imaging (MRI) device, according to some embodiments of the invention;

FIGS. 7A-7B are illustrations of a radiofrequency (RF) channel in a RF shielding door of a neonate incubator, according to some embodiments of the invention.

DETAILED DESCRIPTION OF THE INVENTION

Figures 2A, 2B, 2C:
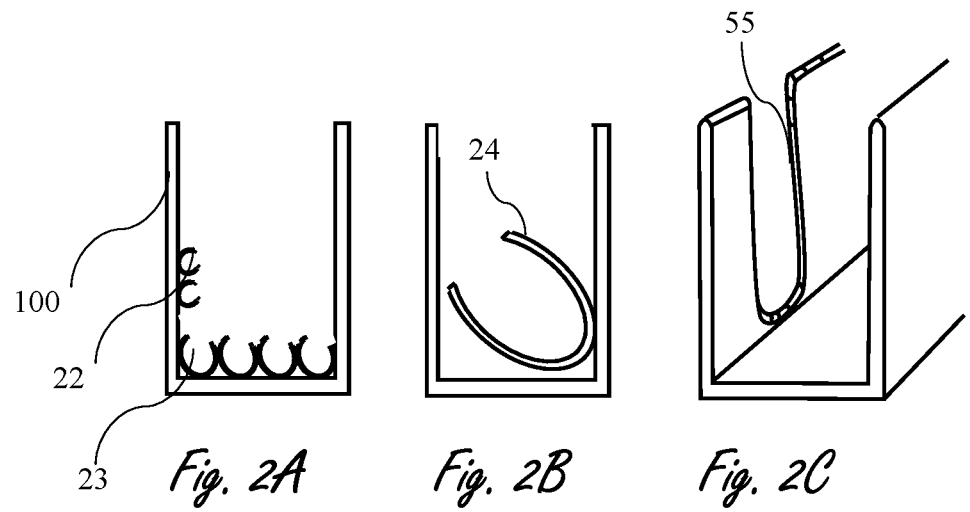
FIG. 2A is a schematic illustration of an embodiment of the profile of the U shaped conduit, a side view schematically illustrating an embodiment of cable holding clips.
FIG. 2B is a schematic illustration of an embodiment of the profile of the U shaped conduit, a side view schematically illustrating a cables and tubes holder.
FIG. 2C is a schematic illustration of an embodiment of the profile of the U shaped conduit, a perspective view schematically illustrating an aperture with curved, smoothed edges.

In the following detailed description of the preferred embodiments, reference is made to the accompanying drawings that form a part hereof, and in which are shown by way of illustration specific embodiments in which the invention may be practiced. It is understood that other embodiments may be utilized and structural changes may be made without departing from the scope of the present invention. The present invention may be practiced according to the claims without some or all of these specific details. For the purpose of clarity, technical material that is known in the technical fields related to the invention has not been described in detail so that the present invention is not unnecessarily obscured. The present invention provides a closure assembly for an MRI bore with means to facilitate the passage of medical equipment.

The essence of the present invention is to provide an incubator's closure assembly intended to hermetically shut an entrance of a MRD bore comprising a U-shaped (e.g., U-shape, C-shape, W-shape, etc.) conduit having an array of distal and proximal sealing walls, both are substantially perpendicular to the longitudinal axis and having upwards and downwards directions, and (ii) a recess in between the walls having length (upwards to downwards direction) and width (distal to proximal direction), wherein each of the proximal wall and the distal wall is having an aperture at opposite directions, and wherein in the recess, the ratio of length to width is greater than a predefined value n.

The present invention further provides an incubator's closure assembly allowing passage of medical equipment from the external environment to the inner volume of the MRD while maintaining EMI shielding toward the exterior space during MRI operation.

The present invention further provides better surveillance and monitoring of the patient during MRI, as the data of the medical devices is protected from EMI. Furthermore, the current invention provides means and methods to MRI a patient without disconnecting medical equipment before after or during imaging. This will further increase safety and wellbeing of patient. The incubator's closure assembly of the present invention further provides shutting of the MRD open bore although patient is connected to medical equipment. This protects the patient from projectile ferromagnetic objects since the closure assembly shuts the MRD bore.

The term 'magnetic resonance imaging device' (MRD), specifically applies hereinafter to any Magnetic Resonance Imaging (MRI) device, any Nuclear Magnetic Resonance (NMR) spectroscope, any Electron Spin Resonance (ESR) spectroscope, any Nuclear Quadruple Resonance (NQR) or any combination thereof. The term, in this invention, also applies to any other analyzing and imaging instruments comprising a volume of interest, such as computerized tomography (CT), ultrasound (US) etc. The MRD hereby disclosed is optionally a portable MRI device, such as the ASPECT-MR Ltd commercially available devices, or a commercially available non-portable device.

The term "closed bore MRI" refers herein after to MRI scanner that has a large cylinder-shape tube inside a MRI magnet.

The term "MRD bore" interchangeably refers hereinafter to a large substantially cylinder-shaped tube of a MRI scanner which is designed to accommodate a patient.

The term "inner space of MRD bore" refers hereinafter to inner volume of a MRI bore.

The term "external environment" refers hereinafter to the external space outside of an MRI scanner.

The term "closure assembly" interchangeably refers hereinafter to any assembly configured to at least partly close an MRI bore opening. Preferably, covering, shutting, closing, and etc. at least one open face of a substantially cylindered bore thereby forming an at least partial partition between the inner space of an MRD bore and the external environment. The term closure assembly is further interchangeable with terms such as closure assembly, shutting assembly, blocking assembly, cover assembly, barring assembly, sealing assembly, partition, border assembly, protective assembly and etc.

The term "value of n" interchangeably refers herein after to the numerical value of the ratio between the length (l) and the width (w) of the recess of the conduit; further the numerical value of n is selected from a group consisting of: $2.5<n<6$, $4<n<6$, $4<n<9$ and any combination thereof.

The term "patient" interchangeably refers herein after to a term selected from a group of: neonate, baby, infant, toddler, child, adolescent, adult, elderly, etc.; further this term refers to person or animal.

The term "medical equipment" interchangeably refers hereinafter to all devices, cables, tubes, connectors, wires, liquid carriers, needles, sensors, etc., that are used by medical staff in association with the patient. This medical equipment is used for various purposes such as life supporting, ventilating, temperature regulating, MRI contras solution injection, monitoring of cardio and breathing rates, viewing the patient, fluids transport, etc.

The term "cables" interchangeably refers hereinafter to all connectors, wires, cords, lines, chains, channel, duct, cable braid etc.

The term "tubes" interchangeably refers hereinafter to all hollow connectors, cables, wires, lines, etc. Typically used for transferring fluid or air.

The term "connected", in reference to the closure assembly parts and modules, interchangeably refers hereinafter to any contact, relation, association, integration, interconnection, joining, interweaving, placing, nesting, layering, etc., of the shutting assembly parts to each other and to a third party.

The term "transparent material" interchangeably refers hereinafter to materials such as, poly-methyl methacrylate, thermoplastic polyurethane, polyethylene, polyethylene terephthalate, isophthalic acid modified polyethylene terephthalate, glycol modified polyethylene terephthalate, polypropylene, polystyrene, acrylic, polyacetate, cellulose acetate, polycarbonate, nylon, glass, polyvinyl chloride, etc. Further this at least a portion of this material may be imbedded with non-transparent materials for means of strength and/ or conductivity such as metallic wires.

The term "equipment ends" refers hereinafter to any equipment that has a longitudinal axis with a distal end and a proximal end. This as a non-limiting example be such as medical life support or monitoring equipment comprising tubes that are connected at their distal end to a patient and on their proximal end to the apparatus body.

The term "visual indicators" interchangeably refers hereinafter to a representation of light in the visible light range of about 380 nanometers to about 740 nm. More generally the terms refer to any light within the visible range that will be noticeable by the user of the invention (light, flashing light, flickering light, blinking light, change of spectrum of colors of light etc.).

The term "audible indicators" interchangeably refers hereinafter to a representation of sound, typically as an electrical voltage. Audible indicators have frequencies in the audio frequency range of roughly 20 to 20,000 Hz (the limits of human hearing). Audible indicators may be synthesized directly, or may originate at a transducer such as a microphone, musical instrument pickup, phonograph cartridge, or tape head.

The term "sensible indicators" interchangeably refers hereinafter to a physical movement of at least a portion of the user interface, which is noticeable to the user (shaking, vibrating, quivering, etc.).

The term "anchor" interchangeably refers hereinafter to a mechanism such as: fastener, draw latch, lock, belt, bolt, grip, bar, bond, clamp, clasp, connection, fixture, link, hook, hasp, buckle, harness, clip, snap, pin, peg, grapnel, band, catch, pin insertion, tube, cable tie; thread, plastic or nylon restraint, concave grove, etc., that is able to hold the position of such as medical equipment, medical equipment cables and tubes, electrical equipment, electrical cables, etc.

The term "placement" interchangeably refers hereinafter to a location for placing one or more cables, tubes, or both. This is achieved by a mean such as a clip, catch, clasp, strip, nest, socket, dent, duct, channel, bridge, band, clamp, harness, concave shape, crater, gap, pocket, cavity, etc.

The term "module" interchangeably refers hereinafter to a structurally independent part, able to be attached and detached (reversibly connected) from the closure assembly. This module is connected itself or by another element in its contour, embedded, integrated, placed, interconnected, etc. to the incubator.

The term "electromagnetic interference" interchangeably refers hereinafter to electromagnetic interference (EMI), and radio-frequency interference (RFI), derived from electromagnetic radiation, electromagnetic induction, magnetism, electrostatic fields etc., that affect any electrical circuit, or imaging device such as MRD, NMR, ESR, NQR, CT, US, etc. This interference is derived from any source natural or artificial such as earth magnetic field, atmospheric noise, moving masses of metal, electrical lines, subways, cellular communication equipment, electrical devices, TV and radio stations, elevators, etc. This interference may interrupt, obstruct, degrade, limit, result in false data, etc., the effective performance of the circuit or device.

The term "electromagnetic shielding" refers hereinafter to a practice or device aimed at reducing the electromagnetic field in a space by blocking the field with barriers made of conductive or magnetic materials. The shielding can reduce the effect of radio waves, electromagnetic fields and electrostatic fields. Shielding is typically applied to isolate devices from the external environment, and to cables to isolate wires from the environment through which the cable runs.

The term "magnetic shielding" refers hereinafter to a practice or device aimed at reducing the magnetic field in a space. This is usually achieved by applying high permeability and low coersivity metal alloys that draw the magnetic shield and contain it such as nickel containing alloys.

The term "active magnetic shielding" refers hereinafter to a practice or device aimed at actively reducing the magnetic field in a space. This is usually achieved by applying a field created by electromagnets to cancel out the ambient field within a volume. This system usually consists of maneuverable coils, magnetic field detectors, and feedback system.

The term "RF shielding" refers hereinafter to electromagnetic shielding that blocks radio frequency electromagnetic radiation.

The term "RF filter" interchangeably refers hereinafter to components designed to filter signals in the MHz to GHz frequency ranges. This frequency range is the range used by most broadcast radio, television, wireless communication. These components exert some kind of filtering on the signals transmitted or received. The filters could be active or passive such as waffle-iron filter, mechanical RF filter, etc. RF filters are usually placed when there is need to pass an electrical wire in or out of an MRD enclosure to ensure that the EMI does not couple on the conductive wiring. These filters could be of passive components such as a combination of inductors and capacitors.

The term "RF attenuation properties" interchangeably refers hereinafter to properties that do not allow passage though of defined RF waves. This could be achieved by means such as waveguides designed to attenuate RF, RF filters, etc.

The term "waveguide cutoff" interchangeably refers hereinafter to a boundary in a system's frequency response at which energy flowing through the system begins to be reduced, attenuated or reflected rather than passing through.

The term "cutoff frequency", (fc) interchangeably refers hereinafter to the frequency beyond which the waveguide no longer effectively contains EMI.

The term "connected" in reference to the incubator's closure assembly and conduit parts and modules, interchangeably refers hereinafter to any contact, relation, association, integration, interconnection, joining, interweaving, placing, nesting, layering, etc., of the closure assembly parts to each other and to a third party.

The term "plurality" interchangeably refers hereinafter to an integer a, when a>1.

The term "RF detection system" interchangeably refers hereinafter to a system designed to detect and alert of the presence of predefined RF waves. This system will typically include a sensor such as an antenna, and an indicator.

According to one embodiment of the present invention, in a magnetic resonance imaging device (MRD) having an open bore extended along the MRD's longitudinal axis with a distal end and proximal end, the bore is terminated by an aperture located in the proximal end, into which a neonate's incubator is inserted, an incubator's closure assembly adapted to hermetically shut the aperture when the incubator is accommodated within the open bore, the closure assembly comprising at least one U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and wherein in the recess, the ratio of length to width is greater than a predefined value n.

According to another embodiment of the invention, an incubator's closure assembly as defined above is disclosed, wherein at least a portion of the conduit faces at least a portion of the MRD open bore when in the incubator's closure assembly is in a closed configuration.

According to another embodiment of the invention, an incubator's closure assembly as defined above is disclosed, wherein the recess longitudinal axis open face is open towards external environment.

According to another embodiment of the invention, an incubator's closure assembly as defined above is disclosed, wherein the cutouts are placed in opposite walls of the conduit in a parallel shifted position thereby not facing each other directly.

According to another embodiment of the invention, an incubator's closure assembly as defined above is disclosed, wherein the conduit is connected in a non-protruding manner to an incubator's closure assembly, thereby, no direct access is provided between the MRD bore and the external environment.

According to another embodiment of the invention, an incubator's closure assembly as defined above is disclosed, wherein the conduit recess is adapted by means of size and shape to permit passage of medical equipment within, from the inner space of MRD bore to the external environment.

According to another embodiment of the invention, an incubator's closure assembly as defined above is disclosed, wherein the conduit cutouts are adapted by means of size and shape to permit passage of medical equipment within, from the inner space of the MRD bore to the external environment.

According to another embodiment of the invention, an incubator's closure assembly as defined above is disclosed, wherein the conduit recess and cutouts are adapted by means of size and shape to permit passage within the conduit of at least one selected from a group consisting of: cable, tube and any combination thereof, from the inner space of MRD bore to the external environment.

According to another embodiment of the invention, an incubator's closure assembly as defined above is disclosed, wherein the conduit recess and cutouts are adapted by means of size and shape to permit passage within the conduit of cables, tubes or both of a plurality of shapes and sizes.

According to another embodiment of the invention, an incubator's closure assembly as defined above is disclosed, wherein the conduit further comprising at least one designated placement for each passing cables, tubes or both, within the conduit;

According to another embodiment of the invention, an incubator's closure assembly as defined above is disclosed, wherein the designated placement is connected in a location within the conduit selected from a group consisting of: recess, cutout, walls and any combination thereof.

According to another embodiment of the invention, an incubator's closure assembly as defined above is disclosed, wherein at least one designated placement is labeled.

According to another embodiment of the invention, an incubator's closure assembly as defined above is disclosed, wherein the conduit further comprising at least one cables and tubes anchor within the conduit.

According to another embodiment of the invention, an incubator's closure assembly as defined above is disclosed, wherein the anchor is connected in a location within the conduit selected from a group consisting of: recess, cutout, walls and any combination thereof.

According to another embodiment of the invention, an incubator's closure assembly as defined above is disclosed, wherein the U-shape is selected from a group consisting of: curved U-shape, polygonal U-shape, symmetrical U-shape, non-symmetrical U-shape, and any combination thereof.

According to another embodiment of the invention, an incubator's closure assembly as defined above is disclosed, wherein the conduit wall along the longitudinal axis is of a shape selected from a group consisting of: straight, curved, polygonal, symmetrical, non-symmetrical and any combination thereof.

According to another embodiment of the invention, an incubator's closure assembly as defined above is disclosed, wherein the conduit open face is adapted by size and shape to enables removal of medical equipment, without detaching it from any of the equipment ends.

According to another embodiment of the invention, an incubator's closure assembly as defined above is disclosed, wherein at least a portion of the conduit cutouts edge comprise a curved profile.

According to another embodiment of the invention, an incubator's closure assembly as defined above is disclosed, wherein at least a portion of the conduit walls edge profiles are of a smoothed finish.

According to another embodiment of the invention, an incubator's closure assembly as defined above is disclosed, wherein at least a portion of the conduit is perforated, further wherein the perforations are of a length and diameter configured as a waveguide RF attenuator, thereby allowing for RF shielding together with light and air penetration into the MRD.

According to another embodiment of the invention, an incubator's closure assembly as defined above is disclosed, wherein the conduit is constructed as a detachable module.

According to another embodiment of the invention, an incubator's closure assembly as defined above is disclosed, wherein the conduit is connected to the incubator's closure assembly at a location comprising at least a portion of the border between the closure assembly and the aperture in MRD bore proximal end.

According to another embodiment of the invention, an incubator's closure assembly as defined above is disclosed, wherein the conduit location enables removal of the equipment when the assembly is retracted from MRD bore, without detaching it from any of the equipment ends.

According to another embodiment of the invention, an incubator's closure assembly as defined above is disclosed, wherein the conduit further comprises an RF filter, thereby permitting electrical wiring to pass into the MRD bore from the external environment.

According to another embodiment of the invention, an incubator's closure assembly as defined above is disclosed, wherein at least a portion of the conduit comprising shielding selected from a group consisting of: magnetic shielding, RF shielding, physical shielding and any combination thereof.

According to another embodiment of the invention, an incubator's closure assembly as defined above is disclosed, wherein at least a portion of the conduit is made of electromagnetic conductive material.

According to another embodiment of the invention, an incubator's closure assembly as defined above is disclosed, wherein the conduit further comprising at least a portion of transparent material.

According to another embodiment of the invention, an incubator's closure assembly as defined above is disclosed, wherein the conduit is configured by means of size, shape and material to attenuate the passage of radio frequencies at a range of the values of X to Y MHz; further wherein the values of X and Y are selected from a group consisting of: X>0 MHz and Y<1000 MHz, X>0 MHz and Y<500 MHz, X>0 MHz and Y<200 MHz and any combination thereof.

According to another embodiment of the invention, an incubator's closure assembly as defined above is disclosed, wherein at least one of the walls is maneuverably connected to said longitudinal wall remaining in a fixed position.

According to another embodiment of the invention, an incubator's closure assembly as defined above is disclosed, wherein the conduit further comprising an RF detector system. Further wherein the RF detection system comprising indicators selected form a group consisting of: audible, sensible, visual and any combination thereof.

According to another embodiment of the invention, an incubator's closure assembly as defined above is disclosed, wherein the assembly is adapted by means of size and shape to be connected to an MRI-compatible cart in connection with an MRI-compatible neonate's cradle.

According to another embodiment of the invention, an incubator's closure assembly as defined above is disclosed, comprising at least one conduit telescopic wall, wherein the wall allows change of the recess width, length, or height as long as the ration between the width and the length of the recess remains greater than a predefined value n.

The present invention further provides, an incubator's closure assembly as defined above is disclosed, comprising a conduit connected to the incubator's closure assembly wherein the connection is configured so the recess longitudinal axis open face is open towards external environment and at least one of the walls connect to the closure assembly, thereby enabling placement of the cables, wires or both without having to thread them through an opening but rather placing them along the conduit.

According to another embodiment of the invention, an incubator's closure assembly as defined above is disclosed, wherein the conduit is connected in a non-protruding manner to an incubator's closure assembly. This is achieved when the cutouts on opposite sides of the conduit are not placed one directly opposite the other. Thereby, no direct access is provided between the MRD bore and the outside.

According to another embodiment of the invention, an incubator's closure assembly as defined above is disclosed, comprising a conduit wherein the conduit open face is wide enough and of a shape giving direct access to the medical equipment too enables removal of the equipment, without detaching it from any of the equipment ends.

According to another embodiment of the invention, an incubator's closure assembly as defined above is disclosed, additionally comprising a step of connecting the conduit wherein at least a portion of the conduit is facing at least a portion of the MRD open bore when in the incubator's closure assembly is in a closed configuration.

According to another embodiment of the invention, an incubator's closure assembly as defined above is disclosed, additionally comprising a step of placing the cutouts in opposite walls of the conduit in a parallel shifted position thereby not facing each other directly.

According to another embodiment of the invention, an incubator's closure assembly as defined above is disclosed, additionally comprising a step of adapting the conduit by means of size and shape to permit passage of medical equipment within, from the inner space of MRD bore to the external environment.

According to another embodiment of the invention, an incubator's closure assembly as defined above is disclosed, additionally comprising a step of adapting by means of size and shape the conduit cutouts to permit passage of medical equipment within, from the inner space of MRD bore to the external environment.

According to another embodiment of the invention, an incubator's closure assembly as defined above is disclosed, additionally comprising a step of adapting by means of size and shape the conduit recess and cutouts to permit passage within the conduit of at least one selected from a group consisting of: cable, tube and any combination thereof, from the inner space of MRD bore to the external environment.

According to another embodiment of the invention, an incubator's closure assembly as defined above is disclosed, wherein the conduit recess is wide, long and deep to enable placement and passage of medical equipment within, from the inner space of MRD bore to the external environment.

According to another embodiment of the invention, an incubator's closure assembly as defined above is disclosed, comprising a conduit recess, wherein the recess holds medical equipment devices such as an infusion bag, life supporting equipment, measuring device for transferred fluids, etc.

According to another embodiment of the invention, an incubator's closure assembly as defined above is disclosed, comprising a conduit wherein the conduit maintains incubator closure assembly shielding such as EMI shielding, RF shielding and physical shielding.

RF and magnetic shield construction create an enclosure in which radio frequency (RF) and/or electromagnetic interference (EMI) is contained and/or prevented from entering. This environment is necessary to ensure proper performance of MRD equipment. When the incubator's closure assembly is in a closed configuration, inserted into the MRD bore, it protects the magnetic field gradient coils from the outer EMI noise, and the MRI RF detecting system from RF noise. Furthermore, when in closed configuration, the closure assembly provides a physical barrier from pulled ferromagnetic objects attracted by the magnetic fields.

According to another embodiment of the invention, an incubator's closure assembly as defined above is disclosed, where at least a portion of the conduit is made of high endurance to impact materials. Such materials may be composed from metal, metal alloys and composite materials and combination thereof. These composites may be GFRP (glass-fiber reinforced plastic) and CFRP (carbon-fiber reinforced plastic).

According to another embodiment of the invention, an incubator's closure assembly as defined above is disclosed, wherein the closure assembly acts as a passive magnetic shield. In order to create an effective non-active magnetic shielding the closure assembly and the conduit may be built from magnetic alloys with high permeability and low coercivity such as different types of Permalloy and Mu-metal.

According to another embodiment of the invention, an incubator's closure assembly as defined above is disclosed, wherein the closure assembly comprising a conduit and the structure it is connected to, form a conductive circuit. This arrangement will serves as an RF shield, further wherein the RF shield is typically made of metal such as copper, galvanized steel, aluminum etc.

According to another embodiment of the invention, an incubator's closure assembly as defined above is disclosed, wherein the conduit closes a conductive circle with the rest of the incubator closure assembly and the MRD.

According to another embodiment of the invention, an incubator's closure assembly as defined above is disclosed, comprising at least a portion of a semi permeable barrier, wherein the barrier is structured like a mesh, web, net, bars, grid, rack, etc. This will maintain air circulation within MDR bore also when an incubator's closure assembly is in a closed configuration. These structures can be made by manufacturing at least a portion of the closure assembly from fibers, nets, rods, of metal or composite materials. Further wherein these grids may be configured to act as waveguides with a cutoff frequency of up to 1 GHz.

According to another embodiment of the invention, an incubator's closure assembly as defined above is disclosed, wherein the incubator's closure assembly comprising a conduit is an all together shape of a round or any other polygonal shape.

According to another embodiment of the invention, an incubator's closure assembly as defined above is disclosed, comprising at least one conduit, wherein the conduit has a cylindrical shape, rectangular shape or any other multifaceted shape.

According to another embodiment of the invention, an incubator's closure assembly as defined above is disclosed, comprising at least one conduit, wherein the conduit has RF attenuation properties. These attenuation properties are reached by means of waveguide, RF filter, waveguide filter and any combination thereof. Waveguide attenuation is configured so that RF frequencies of: 0-1000 MHz, 0-500 MHz, or 0-200 MHz, are below the waveguide cutoff. RF filter can be installed to block RF of defined range. RF filters would provide protection to conductive wiring such as electrical power, data cables, etc. In some embodiments this can be achieved by further perforating the conduit, wherein these perforations are of a length and diameter configured as a waveguide RF attenuator.

According to another embodiment of the invention, an incubator's closure assembly as defined above is disclosed, comprising at least one telescopic wall, wherein the wall allows change of the recess width, length, or height as long as the ration between the width and the length of the recess remains greater than a predefined value n.

Reference is now made to FIG. 1A schematically illustrating, in an out of scale manner, an embodiment of the invention. In this embodiment the U-shaped profile of the conduit (100) comprises walls connected in straight angles to one another.

Reference is now made to FIG. 1B schematically illustrating, in an out of scale manner, an embodiment of the invention. In this embodiment the U-shaped profile of the conduit (100) is a curved profile.

Reference is now made to FIG. 1C schematically illustrating, in an out of scale manner, an embodiment of the invention. In this embodiment the U-shaped profile of the conduit (100) is a non-symmetrical multifaceted shape profile.

Reference is now made to FIG. 1D schematically illustrating, in an out of scale manner, an embodiment of the invention. In this embodiment the conduit wall (16) along its longitudinal axis is a straight planar surface.

Reference is now made to FIG. 1E schematically illustrating, in an out of scale manner, an embodiment of the invention. In this embodiment the conduit wall (17) along its longitudinal axis is a curved surface.

Reference is now made to FIG. 1F schematically illustrating, in an out of scale manner, an embodiment of the invention. In this embodiment the conduit wall (18) along its longitudinal axis is a multi-facet surface. In this shape the length 11 measured from point A to point B, is shorter than the length measurement 12 that is the actual length along which the cables or tubes (150) are passed. Because the RF attenuation proprieties are calculated using the accumulating length of the multi faced wall (18) as in 12, 11 can be shorter and the conduit will still maintain the ratio of length to width to be greater than a predefined value n. This allows for embodiments having different sized conduits.

Reference is now made to FIG. 2A schematically illustrating, in an out of scale manner, an embodiment of the invention. In this embodiment the conduit (100) further comprises one or a plurality designated placements (22-23) for organizing the cables, tubes or both. This placement is rigid, flexible, or partly flexible. This placement is a clips, holder, organizer, clasp, catch, fastener, clamp, harness, nest, band, belt, strap, etc. In addition these placements are of various sizes. Further this placement may be labeled to ease finding a specific tube. These placements will also reduce the accidental movement of the cables within the conduit, reducing detachment from the patient accidents and reducing friction of the cables, tubes or both on the conduit. Each placement holds one or more cables, tubes or both.

Reference is now made to FIG. 2B schematically illustrating, in an out of scale manner, an embodiment of the invention. In this embodiment the conduit (100) further comprises one or a plurality designated anchors (24) for organizing all of the cables, tubes or both together. This anchor is rigid, flexible, or partly flexible. This anchor is a clips, holder, organizer, clasp, catch, fastener, clamp, harness, nest, band, belt, strap etc. In addition in some embodiments the anchor is a sizable one. The anchor will reduce the accidental movement of the cables within the conduit, reducing detachment from the patient accidents and reducing friction of the cables, tubes or both on the conduit.

Reference is now made to FIG. 2C schematically illustrating, in an out of scale manner, an embodiment of the invention. In this embodiment the conduit (100) comprises a cutout (55) for the passing of medical equipment having a smooth curved finish to ease the sliding of the cables, tubes or both, while reducing friction. High friction over time may damage the cables, tubes or both, further leading to excessive maintenance. Using damaged cables, tubes or both could lead to health complications.

Figure 2D:
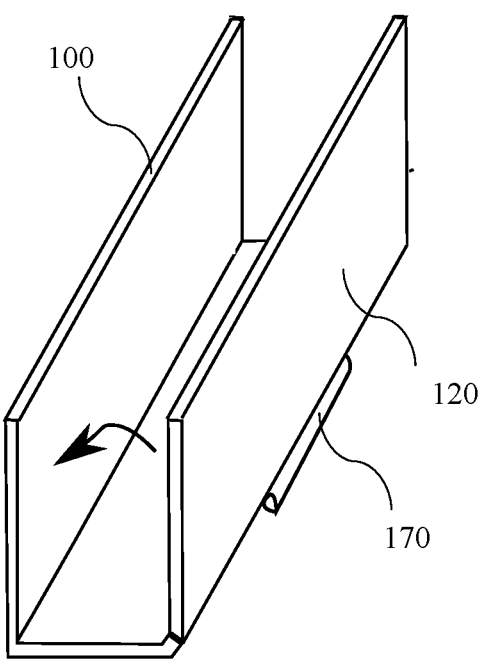
FIG. 2D is a schematic illustration of an embodiment of the profile of the U shaped conduit, a perspective view schematically illustrating a hinge like structure enabling movement of a wall of the conduit.

Reference is now made to FIG. 2D schematically illustrating, in an out of scale manner, an embodiment of the invention. In this embodiment the conduit (100) distal wall (120) is maneuverably connected to the longitudinal axis wall. In this embodiment the wall is able to move in an angle pivoted on the hinge (170), towards the passing cables, tubes or both thereby securing their position. This connection with a means such as a hinge, joint, clamp, hook, clasp, bracket, lock, grasp, slide track, threading module, screwing module, link, fold, turning module, etc.

Reference is now made to FIG. 3A schematically illustrating, in an out of scale manner, an embodiment of the invention presenting a conduit (100) constructed of a multi faced hollow frame, that has a cutout face on one side. Further in this embodiment the conduit includes a rectangular cutout facing the MRD bore (50) and another rectangular cutout (60) facing the exterior of the MRD bore. These cutouts may be of a shape such as rectangular, circular, elliptical, compound shape, symmetrical, non-symmetrical, curved, polygonal, multifaceted, etc.

Reference is now made to FIG. 3B schematically illustrating, in an out of scale manner, an embodiment of the invention presenting an exemplary arrangement of the closure assembly where the conduit (100) is connected to the side contour of the closure assembly (200). This embodiment enables the tubes and wires of the medical equipment to pass along the side of the closure so that during use there is no need to disconnect the patient in order to close or open the MRD bore. This embodiment allows fast mobility of the patient when needed.

Reference is now made to FIG. 3C schematically illustrating, in an out of scale manner, an embodiment of the invention presenting a detachable module conduit (100) having an interconnected part (120) fitting to other components such as patient bed, gurney, operating table, ambulance gear, transport incubator, etc. This allows for easy transport of the patient connected to medical equipment to various accommodations.

Reference is now made to FIG. 3D schematically illustrating, in an out of scale manner, an embodiment of the invention presenting a conduit (100) constructed of a multi faced hollow frame, that has a cutout face on one side. Further in this embodiment the conduit includes a rectangular cutout facing the MRD bore (50) and another circular cutout (60) facing the exterior of the MRD bore. Further schematically presented is an exemplary tube (150) passing through the conduit.

Reference is now made to FIG. 3E schematically illustrating, in an out of scale manner, an embodiment of the invention presenting a conduit (100) where the exemplary tube (150) passes through the bottom cutout face (90) of the conduit and a rectangular recess (50) in the conduit wall.

Figure 4A:
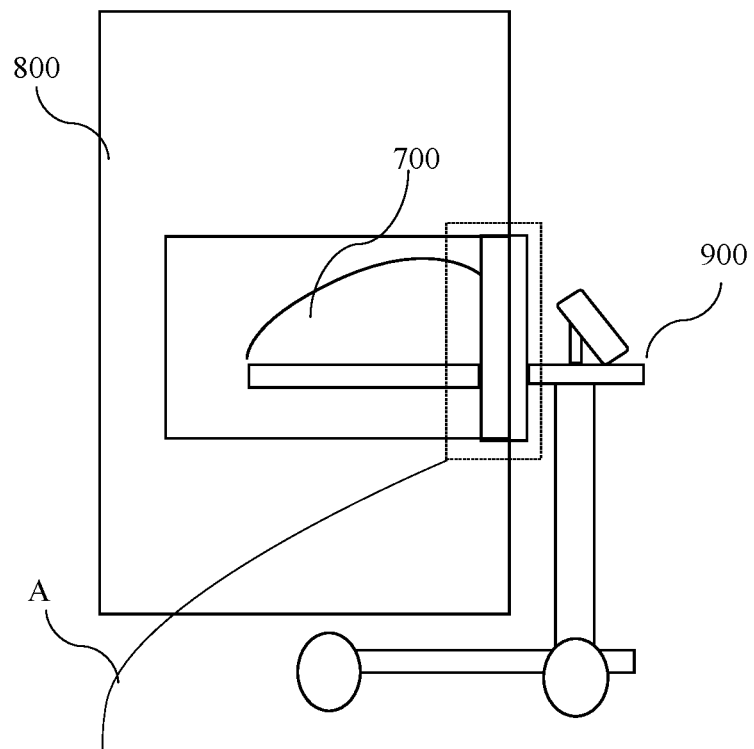
FIG. 4A is a schematic illustration of a general side view of one embodiment of an MRI cart connected to a neonate incubator installed with an embodiment of a shutting assembly for an MRD bore.

Reference is now made to FIG. 4A schematically illustrating, in an out of scale manner, an embodiment of the invention presenting an exemplary arrangement of the closure assembly connected to an MRI cart (900) harboring a neonate cradle (700), as depicted in IL patent application No. 226488, dated 21 May 2013, titled MRI-compatible neonate's cradle, and is incorporated in its entirety, where the conduit (100) is connected to the side contour of the closure assembly. In this configuration all of the closure assembly parts are in fixed position relative to one another, whereas shutting the MRD bore originates from movement of the cart harboring the closure mechanism. The closure assembly could harbor a latch to fasten the location of the closure assembly relative to the cart and/or the MRD bore.

Figure 4B:
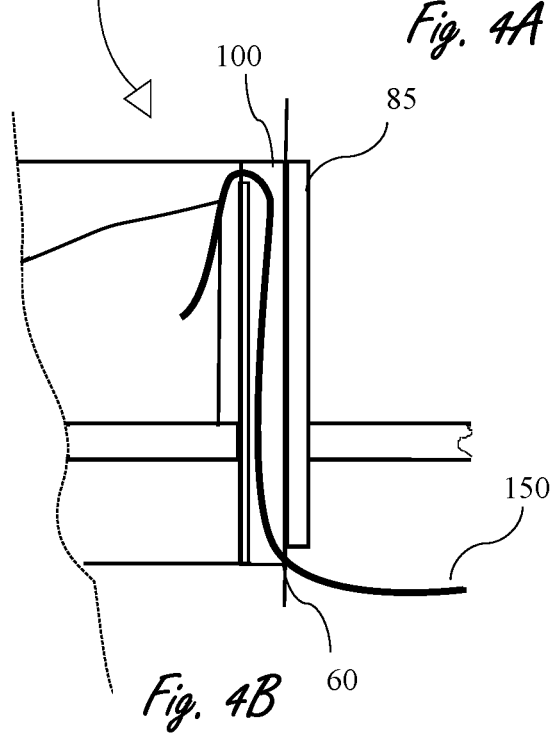
FIG. 4B is a schematic illustration of an embodiment of the closure assembly having a more detailed illustration of area A in FIG. 4A.

Reference is now made to FIG. 4B schematically illustrating, in an out of scale manner, an embodiment of the invention presenting an enlargement of the area 'A' in FIG. 4A. In this embodiment the conduit (100) is attached to the contour of the closure assembly allowing the exemplary tube (150) to be placed along the side of the assembly so that no disconnection of the tube is needed when opening and closing the MDR bore. The exemplary tube exits the conduit through a cutout (60). The elevated face of the conduit (85) maintains the RF attenuating properties of the closure mechanism.

Figure 5A:
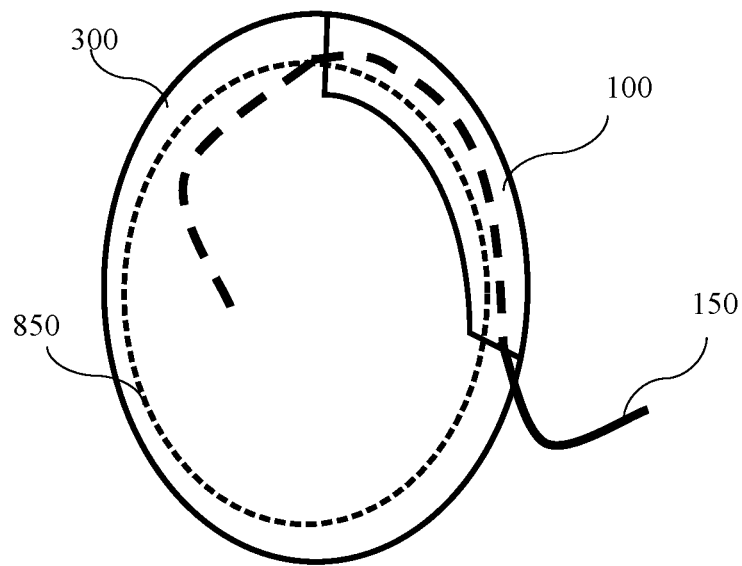
FIG. 5A is a schematic illustration of a circular embodiment of the shutting assembly.

Reference is now made to FIG. 5A schematically illustrating, in an out of scale manner, a circular embodiment of the invention (300), completely covering the opening of a cylindrical MRD bore (850), comprising an arch like conduit (100). An exemplary tube (150) is passed through the conduit placed along a part of the side contour of the closure assembly.

Figure 5B:
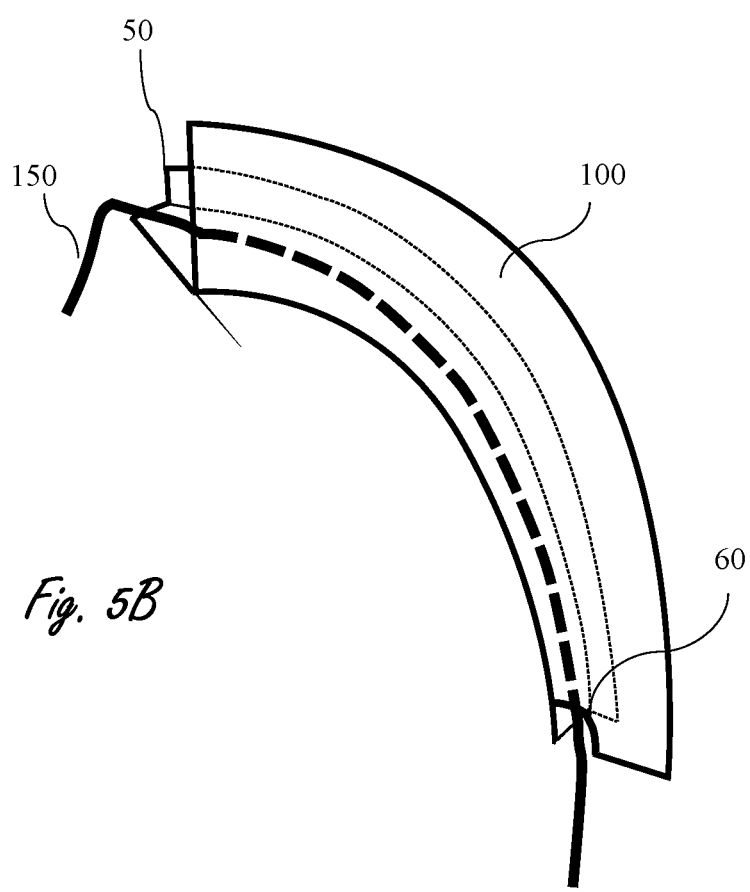
FIG. 5B is a schematic illustration of a conduit as part of a circular embodiment of a closure assembly.

Reference is now made to FIG. 5B schematically illustrating, in an out of scale manner, an embodiment of the invention presenting an arch like conduit (100), with designated cutouts for entry (50) and exiting (60) an exemplary tube (150), in a manner that does not force disconnection of the tube on either side.

According to another embodiment of the invention, a method for RF shielding an MRD from the external environment generated EMI, and RF shielding the external environment from the MRD generated EMI, by providing an RF shielding conduit, comprising steps of: (a) obtaining an MRD, and an incubator connected to an incubator's closure assembly comprising at least one U-shaped RF shielding conduit, the conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and in the recess, the ratio of length to width is greater than a predefined value n; (b) inserting the incubator containing patient into MRD bore, thereby shutting MRD bore with incubator closure assembly; (c) imaging patient; (d) opening MRI bore by extracting the incubator; and (e) extracting patient, wherein the conduit is connected in a non-protruding manner to an incubator's closure assembly, thereby, no direct access is provided between the MRD bore and the external environment.

According to another embodiment of the invention, a method as defined above is disclosed, additionally comprising a step of connecting the conduit wherein at least a portion of the conduit is covering at least a portion of the MRD open bore when in the incubator's closure assembly is in a closed configuration.

According to another embodiment of the invention, a method as defined above is disclosed, additionally comprising a step of placing the cutouts in opposite walls of the conduit in a parallel shifted position thereby not facing each other directly.

According to another embodiment of the invention, a method as defined above is disclosed, additionally comprising a step of adapting the conduit by means of size and shape to permit passage of medical equipment within, from the inner space of MRD bore to the external environment.

According to another embodiment of the invention, a method as defined above is disclosed, additionally comprising a step of adapting by means of size and shape the conduit cutouts to permit passage of medical equipment within, from the inner space of MRD bore to the external environment.

According to another embodiment of the invention, a method as defined above is disclosed, additionally comprising a step of adapting by means of size and shape the conduit recess and cutouts to permit passage within the conduit of at least one selected from a group consisting of: cable, tube and any combination thereof, from the inner space of MRD bore to the external environment.

According to another embodiment of the invention, a method as defined above is disclosed, additionally comprising a step of adapting by means of size and shape the conduit recess and cutouts to permit passage within the conduit of cables, tubes or both of a plurality of shapes and sizes.

According to another embodiment of the invention, a method as defined above is disclosed, additionally comprising a step of forming at least a portion of the conduit to be perforated, further wherein the perforations are of a length and diameter configured as a waveguide RF attenuator, thereby allowing for RF shielding together with light and air penetration into the MRD.

According to another embodiment of the invention, a method as defined above is disclosed, additionally comprising a step of constructing the conduit as a detachable module.

According to another embodiment of the invention, a method as defined above is disclosed, additionally comprising a step of connecting the conduit to the incubator's closure assembly at a location comprising at least a portion of the border between the closure assembly and the aperture in MRD bore proximal end.

According to another embodiment of the invention, a method as defined above is disclosed additionally comprising a step of connecting an RF filter to the conduit, thereby permitting electrical wiring to pass into MRD bore from the external environment.

According to another embodiment of the invention, a method as defined above is disclosed, additionally comprising a step of forming at least a portion of the conduit from electromagnetic conductive material.

According to another embodiment of the invention, a method as defined above is disclosed, additionally comprising a step of configuring the conduit by means of size, shape and material to attenuate the passage of radio frequencies at a range of the values of X to Y MHz; further wherein the values of X and Y are selected from a group consisting of: X>0 MHz and Y<1000 MHz, X>0 MHz and Y<500 MHz, X>0 MHz and Y<200 MHz and any combination thereof.

According to another embodiment of the invention, a method as defined above is disclosed, additionally comprising a step of adapting the incubator's closure assembly by means of size and shape to connect an MRI-compatible cart in connection with an MRI-compatible neonate's cradle.

According to another embodiment of the invention, a method for manufacturing an incubator's closure assembly comprising a U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), consisting steps of: (a) obtaining an incubator closure assembly; (b) defining dimensions of a U-shaped conduit to fit passage of medical equipment within; (c) defining the recess, so that the ratio of length to width is greater than a predefined value n; (d) forming the conduit; (e) forming cutouts at opposite directions in the distal and proximal walls of the conduit; (f) connecting the conduit to incubator's closure assembly so the open longitudinal face is open towards the external environment; wherein the conduit is connected in a non-protruding manner to an incubator's closure assembly, thereby, no direct access is provided between the MRD bore and the outside.

According to another embodiment of the invention, a method as defined above is disclosed, additionally comprising a step of connecting the conduit wherein at least a portion of the conduit is covering at least a portion of the MRD open bore when in the incubator's closure assembly is in a closed configuration.

According to another embodiment of the invention, a method as defined above is disclosed, additionally comprising a step of placing the cutouts in opposite walls of the conduit in a parallel shifted position thereby not facing each other directly.

According to another embodiment of the invention, a method as defined above is disclosed, additionally comprising a step of adapting the conduit by means of size and shape to permit passage of medical equipment within, from the inner space of MRD bore to the external environment.

According to another embodiment of the invention, a method as defined above is disclosed, additionally comprising a step of adapting by means of size and shape the conduit cutouts to permit passage of medical equipment within, from the inner space of MRD bore to the external environment.

According to another embodiment of the invention, a method as defined above is disclosed, additionally comprising a step of adapting by means of size and shape the conduit recess and cutouts to permit passage within the conduit of at least one selected from a group consisting of: cable, tube and any combination thereof, from the inner space of MRD bore to the external environment.

According to another embodiment of the invention, a method as defined above is disclosed, additionally comprising a step of adapting by means of size and shape the conduit recess and cutouts to permit passage within the conduit of cables, tubes or both of a plurality of shapes and sizes.

According to another embodiment of the invention, a method as defined above is disclosed, additionally comprising a step of connecting at least one designated placement for each passing cables, tubes or both, within the conduit;

According to another embodiment of the invention, a method as defined above is disclosed, additionally comprising a step of connecting at least one designated placement in a location within the conduit selected from a group consisting of: recess, cutout, walls and any combination thereof.

According to another embodiment of the invention, a method as defined above is disclosed, additionally comprising a step of attaching a label to at least one designated placement is labeled.

According to another embodiment of the invention, a method as defined above is disclosed, additionally comprising a step of connecting at least one cables and tubes anchor within the conduit.

According to another embodiment of the invention, a method as defined above is disclosed, additionally comprising a step of connecting the anchor in a location within the conduit selected from a group consisting of: recess, cutout, walls and any combination thereof.

According to another embodiment of the invention, a method as defined above is disclosed, additionally comprising a step of forming the U-shape conduit in a shape selected from a group consisting of: curved U-shape, polygonal U-shape, symmetrical U-shape, non-symmetrical U-shape, and any combination thereof. Additionally or alternatively, the conduit shape can be substantially U-shaped, C-shaped, V-shaped, W-shaped, E-shaped, N-shaped, G-shaped and etc. In an embodiment, the shape of the conduit can change along the longitudinal axis of the conduit, thereby forming a one geometrical shape at one end, and at least one second geometrical shape at any point along the longitudinal axis. Additionally or alternatively, the conduit can differ in opening size and the ratio of length to width along the longitudinal axis of the conduit. In this embodiment more than one range of waveguide cutoff can be provided according to the shape and opening size.

According to another embodiment of the invention, a method as defined above is disclosed, additionally comprising a step of forming the U-shaped conduit wall along the longitudinal axis in a shape selected from a group consisting of: straight, curved, polygonal, symmetrical, non symmetrical and any combination thereof.

According to another embodiment of the invention, a method as defined above is disclosed, additionally comprising a step of adapting by means of size and shape the conduit open face to enable removal of the equipment, without detaching it from any of the equipment ends.

According to another embodiment of the invention, a method as defined above is disclosed, additionally comprising a step of forming at least a portion of the conduit cutouts edge in a curved profile.

According to another embodiment of the invention, a method as defined above is disclosed, additionally comprising a step of forming at least a portion of the conduit walls edge profiles in a smoothed finish. This will enable flowing movement of the cable or tube across the edge of the conduit when inserting or extracting it from the conduit, further preventing wear and tear of the medical equipment portions.

According to another embodiment of the invention, a method as defined above is disclosed, additionally comprising a step of forming at least a portion of the conduit to be perforated, further wherein the perforations are of a length and diameter configured as a waveguide RF attenuator, thereby allowing for RF shielding together with light and air penetration into the MRD.

According to another embodiment of the invention, a method as defined above is disclosed, additionally comprising a step of constructing the conduit as a detachable module.

According to another embodiment of the invention, a method as defined above is disclosed, additionally comprising a step of connecting the conduit to the incubator's closure assembly at a location comprising at least a portion of the border between the closure assembly and the aperture in MRD bore proximal end.

According to another embodiment of the invention, a method as defined above is disclosed, additionally comprising a step of locating the to enable removal of the equipment when the assembly is retracted from MRD bore, without detaching it from any of the equipment ends.

According to another embodiment of the invention, a method as defined above is disclosed, additionally comprising a step of connecting an RF filter to the conduit, thereby permitting electrical wiring to pass into MRD bore from the external environment.

According to another embodiment of the invention, a method as defined above is disclosed, additionally comprising a step of shielding at least a portion of the conduit selected from a group consisting of: magnetic shielding, RF shielding, physical shielding and any combination thereof.

According to another embodiment of the invention, a method as defined above is disclosed, additionally comprising a step of forming at least a portion of the conduit from electro magnetic conductive material.

According to another embodiment of the invention, a method as defined above is disclosed, additionally comprising a step of forming at least a portion of the conduit from transparent material.

According to another embodiment of the invention, a method as defined above is disclosed, additionally comprising a step of configuring the conduit by means of size, shape and material to attenuate the passage of radio frequencies at a range of the values of X to Y MHz; further wherein the values of X and Y are selected from a group consisting of: X>0 MHz and Y<1000 MHz, X>0 MHz and Y<500 MHz, X>0 MHz and Y<200 MHz and any combination thereof.

According to another embodiment of the invention, a method as defined above is disclosed, additionally comprising a step of maneuverably connecting the distal wall, the proximal wall or both to the longitudinal wall remaining in a fixed position.

According to another embodiment of the invention, a method as defined above is disclosed, additionally comprising a step of connecting an RF detector system. Further wherein the RF detection system comprising indicators selected form a group consisting of: audible, sensible, visual and any combination thereof.

According to another embodiment of the invention, a method as defined above is disclosed, additionally comprising a step of adapting the incubator's closure assembly by means of size and shape to connect an MRI-compatible cart in connection with an MRI-compatible neonate's cradle.

According to another embodiment of the invention, a standard of care protocol is disclosed for magnetic resonance imaging a patient placed within incubator, connected to medical equipment, whilst not leaking RF into the MRD and from the MRD, further enabling a one step insertion or exertion of patient from MRD without detaching connected medical equipment, characterized by providing an incubator's closure assembly adapted to hermetically shut a magnetic resonance imaging device (MRD) having an open bore extended along the MRD's longitudinal axis with a distal end and proximal end, the bore is terminated by an aperture located in the proximal end, into which a neonate's incubator is inserted, when the incubator is accommodated within the open bore, the closure assembly comprising a U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall is having an aperture at opposite directions, wherein at least one of the following is held true: (a) the average number of patient's health complications due to multi-step extraction of patients from MRD in an emergency is z times higher than when utilizing the incubator's closure assembly, z is equal or greater than 1.05; (b) the average number of MRD associated patient's health complications due to detaching and attaching medical equipment to the patient is i times higher than when utilizing the incubator's closure assembly, i is equal or greater than 1.05; (c) the average number of insurable claims of a selected from a group consisting of: manufacturer, handler, user, operator, medical care personal, medical facility, medical facility management or any combination thereof when utilizing the incubator's closure assembly is m times lower than patient MRI associated insurable claims; m is equal or greater than 1.05; (d) the average number of repeated MRI due to EMI created artifacts when utilizing the incubator's closure assembly is p times lower than the average number of repeated MRI; p is equal or greater than 1.05; (e) the average number of reported incidents of EMI interfering with medical equipment during MRI when utilizing the incubator's closure assembly is 5 times lower than the average number of reported incidents of EMI interfering with medical equipment during MRI; 5 is equal or greater than 1.05; (f) the average stress levels of patients measured by the average levels of the patient salival cortisol during MRI when utilizing the incubator's closure assembly is t times lower than the average stress levels of patients during MRI; t is equal or greater than 1.05; (g) the average number of patient's health complications due to artifacts in MRD images caused by EMI is r times higher than when utilizing the incubator's closure assembly; r is equal or greater than 1.05; (h) the average number of patient's health complications due EMI interfering with medical equipment is u times higher than when utilizing the incubator's closure assembly; u is equal or greater than 1.05; and (i) the average number of EMI incidents of interfering with imaging equipment is w times higher than when utilizing the incubator's closure assembly; w is equal or greater than 1.05.

The present invention provides a magnetic resonance imaging device (MRD) having an open bore extended along the MRD's longitudinal axis with a distal end and proximal end, the bore is terminated by an aperture located in the proximal end, into which a neonate's incubator is inserted, an incubator's closure assembly adapted to hermetically shut the aperture when the incubator is accommodated within the open bore, the closure assembly comprising at least one U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and wherein in the recess, the ratio of length to width is greater than a predefined value n; further wherein the conduit is connected in a non-protruding manner to an incubator's closure assembly, thereby, no direct access is provided between the MRD bore and the external environment; further wherein the conduit cutouts are adapted by means of size and shape to permit passage of medical equipment within, from the inner space of the MRD bore to the external environment; further wherein the conduit wall along the longitudinal axis is of a shape selected from a group consisting of: straight, curved, polygonal, symmetrical, non-symmetrical and any combination thereof; further wherein the conduit open face is adapted by size and shape to enable removal of at least a portion of medical equipment passing within the conduit, without detaching it from any of the equipment ends.

The present invention provides in a magnetic resonance imaging device (MRD) having an open bore extended along the MRD's longitudinal axis with a distal end and proximal end, the bore is terminated by an aperture located in the proximal end, into which a neonate's incubator is inserted, an incubator's closure assembly adapted to hermetically shut the aperture when the incubator is accommodated within the open bore, the closure assembly comprising at least one U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and wherein in the recess, the ratio of length to width is greater than a predefined value n; further wherein the conduit is connected in a non-protruding manner to an incubator's closure assembly, thereby, no direct access is provided between the MRD bore and the external environment; further wherein the conduit cutouts are adapted by means of size and shape to permit passage of medical equipment within, from the inner space of the MRD bore to the external environment; further wherein the conduit wall along the longitudinal axis is of a shape selected from a group consisting of: straight, curved, polygonal, symmetrical, non-symmetrical and any combination thereof; further wherein at least a portion of the conduit comprising shielding selected from a group consisting of: magnetic shielding, RF shielding, physical shielding and any combination thereof; further wherein at least one of the walls is maneuverably connected to the longitudinal wall remaining in a fixed position; further wherein the assembly is adapted by means of size and shape to be connected to an MRI-compatible cart in connection with an MRI-compatible neonate's cradle.

The present invention provides a magnetic resonance imaging device (MRD) having an open bore extended along the MRD's longitudinal axis with a distal end and proximal end, the bore is terminated by an aperture located in the proximal end, into which a neonate's incubator is inserted, an incubator's closure assembly adapted to hermetically shut the aperture when the incubator is accommodated within the open bore, the closure assembly comprising at least one U-shaped conduit having (i) an array of distal and proximal sealing walls, both are substantially perpendicular to the longitudinal axis and having upwards and downwards directions, and (ii) a recess in between the walls having length (upwards to downwards direction) and width (distal to proximal direction), each of the proximal wall and the distal wall comprising a cutout at opposite directions, and wherein in the recess, the ratio of length to width is greater than a predefined value n; further wherein the conduit is connected in a non-protruding manner to an incubator's closure assembly, thereby, no direct access is provided between the MRD bore and the external environment; further wherein the conduit cutouts are adapted by means of size and shape to permit passage of medical equipment within, from the inner space of the MRD bore to the external environment; further wherein the assembly is adapted by means of size and shape to be connected to an MRI—compatible cart in connection with an MRI—compatible neonate's cradle.

FIGS. 6A-6B are illustrations of a neonate incubator 200 for positioning a neonate 90 within a magnetic resonance imaging (MRI) device, according to some embodiments of the invention. FIG. 6A provides an isometric view and a top view of the neonate incubator 200 with an access door 203 in closed state (at the top and the bottom of FIG. 6A, respectively). FIG. 6B provides an isometric view of the neonate incubator 200 with an access door 203 in open state.

The neonate incubator 200 can include a proximal end 201 and a distal end 202. The neonate incubator 200 can include an access door 203. The access door 203 can include, for example, a first hinged panel 203a and/or a second hinged panel 203b (e.g., as shown in FIGS. 6A-6B). The first and/or the second hinged panels 203a, 203b, respectively, can be opened, for example, laterally with respect to a longitudinal axis 204 of the neonate incubator 200 (e.g., as shown in FIG. 6B), to, for example, allow a positioning of a neonate 90 within an interior chamber 205 of the incubator. The neonate incubator 200 can be inserted into a bore of a MRI device (not shown) via the proximal end 201 (e.g., as indicated by a dashed arrows in FIGS. 6A-6B).

The neonate incubator 200 can include a radiofrequency (RF) shielding door 210. The RF shielding door 210 can be coupled to the distal end 202 of the neonate incubator 200. The RF shielding door 210 can mate with the bore of the MRI device to, for example, provide a RF shielding of the MRI device. The RF shielding of the MRI device can include preventing from a RF radiation emitted by the MRI device from exiting the bore and/or from an external radiation (e.g., emitted by a medical equipment positioned in a vicinity of the MRI device) from entering the bore of the MRI device.

The incubator 200 can include a RF channel (e.g., conduit) 220. The RF channel 220 can extend from the interior chamber 205 of the neonate incubator 200 through the RF shielding door 210 along an axis that is substantially parallel to the longitudinal axis of the incubator. The RF channel 220 can have a length to width ratio (e.g., a length to an inner diameter ratio) of at least 5:1 to provide the RF shielding of the MRI device.

Medical conditions of the neonate 90 can require, for example, a continuous connection of the neonate 90 to medical equipment while undergoing a MRI scan. The RF channel 220 can enable a passage of a tubing 95 of medical equipment (e.g., that can be connected to the neonate 90) from the interior chamber 205 to an environment that is external to the neonate incubator 200 (e.g., as shown in FIGS. 6A-6B) while eliminating a need to disconnect the tubing 95 from the neonate 90 and/or from medical equipment.

In various embodiments, the RF channel 220 is positioned within the interior chamber 205 of the neonate incubator 200 (e.g., as shown in FIGS. 6A-6B) and/or at least a portion of the RF channel 220 protrudes from the RF shielding door 210 towards the environment that is external to the neonate incubator 200 (not shown).

Figure 7A:
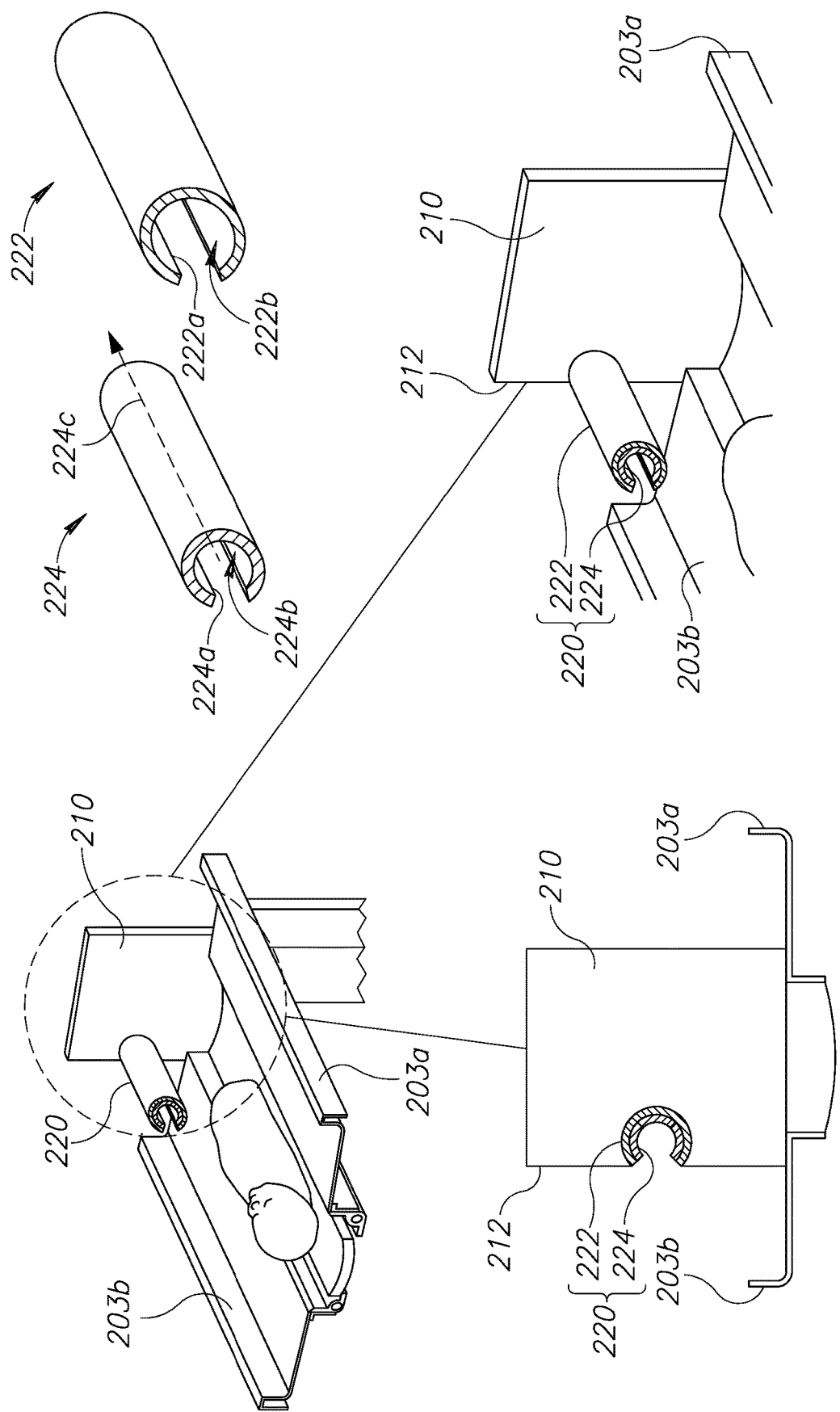

FIGS. 7A-7B are illustrations of a radiofrequency (RF) channel 220 in a RF shielding door 210 of a neonate incubator 200, according to some embodiments of the invention. FIG. 7A and FIG. 7B illustrate the RF channel 220 in open and closed states, respectively.

The RF channel (e.g., conduit) 220 can include a first cylindrical shell 222. The first cylindrical shell 222 can include a first cutout 222a in a longitudinal direction along the shell and/or a substantially hollow interior 222b. The first cutout 222a can be positioned adjacent to an outer edge 212 of the closure assembly 210 (e.g., as shown in FIG. 7A).

The RF channel 220 can include a second cylindrical shell 224. The second cylindrical shell 224 can have a second cutout 224a in a longitudinal direction along the shell and/or a substantially hollow interior 224b. The second cylindrical shell 224 can be positioned coaxially within the substantially hollow interior 222b of the first cylindrical shell 222. The second cylindrical shell 224 can be designed to be rotated about a longitudinal axis 224c of the second cylindrical shell 224.

The RF channel 220 can be opened by, for example, substantially aligning the second cutout 224a with the first cutout 222a (e.g., by rotating the second cylindrical shell 224 about the longitudinal axis 224c). The tubing 95 of medical equipment (e.g., that can extend from the interior chamber 205 to the environment that is external to the neonate incubator 200) can thereby be inserted into the substantially hollow interior 224b of the second cylindrical shell 224 via the first and the second cutouts 222a, 224a, respectively (e.g., as shown in FIG. 7A), e.g., without a need to disconnect the tubing 95 from the neonate 90 and/or from medical equipment to position the neonate in the incubator.

The RF channel 220 can be closed by, for example, shifting the second cutout 224a to a position that is substantially opposite with respect to the first cutout 222a (e.g., by rotating the second cylindrical shell 224 about the longitudinal axis 224c). The RF channel 210 can thereby enclose the tubing 95 of medical equipment extending from the interior chamber 205 to the environment that is external to the neonate incubator 200 (e.g., as shown in FIG. 7B) while providing the RF shielding of the MRI device.

In some embodiments, the RF channel 220 includes at least one holder (e.g., placement) to hold the tubing 95 of medical equipment passing through the RF channel 220 in a predetermined position (not shown). In various embodiments, each of the holders can be at least one of the placements 22, placements 23 and/or placements 24 as described in detail with respect to FIGS. 2A-2B. Holders 230 can be attached, for example, along the substantially hollow interior 224b of the second cylindrical shell 224.

One advantage of the present invention (e.g., RF channel 220) can include enabling a passage of a tubing of medical equipment (e.g., tubing 95) from an interior of a neonate incubator (e.g., neonate incubator 200) without bending the tubing, thereby reducing a risk of kinking of the tubing, which can cause for example, flow restriction, and/or allowing a usage of tubing that cannot be bent.

Another advantage of the present invention (e.g., RF channel 220) can include eliminating a contact between a tubing of medical equipment (e.g., tubing 95) and a patient (e.g., neonate 90) prior to an entry of the tubing into the patient's body (e.g., mouth of the neonate 90 as shown in FIGS. 6A-6B).

Another advantage of the present invention (e.g., RF channel 220) can include simplifying a design and/or a construction of a RF shielding door (e.g., RF shielding door 210) of a neonate incubator (e.g., neonate incubator 200), such that, for example, only one hole in the RF shielding door is needed.

Figure 8:
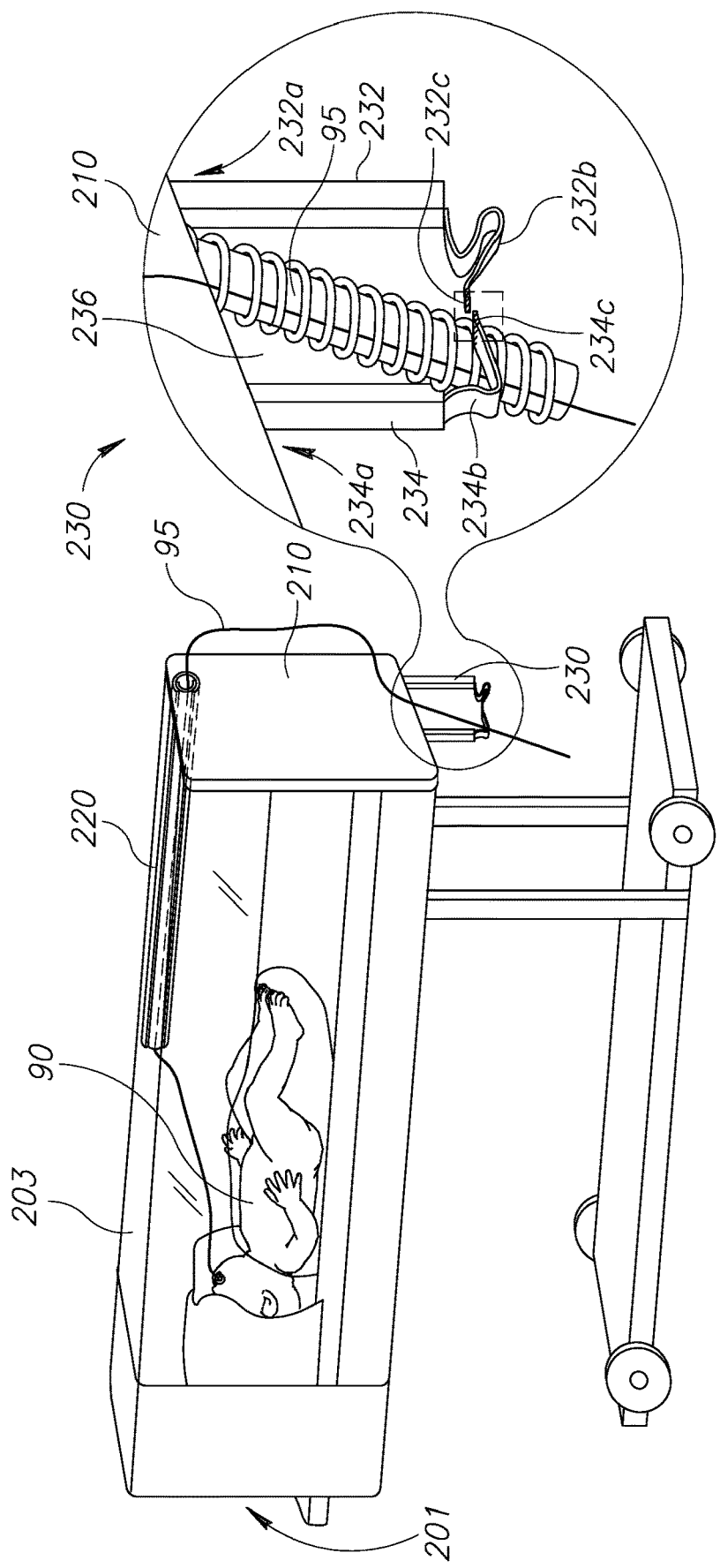
FIG. 8 is an illustration of a holder for a tubing of medical equipment attached to a radiofrequency (RF) shielding door of a neonate incubator, according to some embodiments of the invention.

FIG. 8 is an illustration of a holder 230 for a tubing 95 of medical equipment attached to a radiofrequency (RF) shielding door 210 of a neonate incubator 200, according to some embodiments of the invention.

The neonate incubator 200 can include at least one holder 230 (e.g., placement) connected to the RF shielding door 210. Holder 230 can hold the tubing 95 of medical equipment extending from the RF shielding door 210 in a predetermined position (e.g., as shown in FIG. 8). In various embodiments, the holder 230 is at least one of the placements 22, placements 23 and/or placements 24 as described in detail with respect to FIGS. 2A-2B.

The holder 230 can include a first flexible element 232 having a first proximal end 232a and a first distal end 232b. The holder 230 can include a second flexible element 234 having a second proximal end 234a and a second distal end 234b. The first and/or second flexible elements 232, 234, respectively, can have a substantially L-shape. The first and/or second flexible elements 232, 234, can be attached to the RF shielding door 210 of the neonate incubator 200 at the first and second proximal ends 232a, 234a, respectively.

In some embodiments, at least a portion of the first distal end 232b of the first flexible element 232 overlaps with at least a portion of the second distal end 234b of the second flexible element 234, forming thereby a first overlapping portion 232c and a second overlapping portion 234c, respectively. The holder 230 can include a gap 236. The gap 236 can be bounded by the first and second flexible elements 232, 234, respectively and/or a portion of the RF shielding door 210 between the first and second proximal ends 232a, 234a of the first and second flexible elements 232, 234, respectively (e.g., as shown in FIG. 8).

In various embodiments, the first overlapping portion 232c is closer to the RF shielding door 210 than the second overlapping portion 234c (e.g., as shown in FIG. 8) and/or the second overlapping portion 234c is closer to the RF shielding door 210 than the first overlapping portion 232c (not shown).

The tubing 95 of medical equipment that can extend, for example, from the RF shielding door 210, can be positioned within the gap 236 of the holder 230 by, for example, pushing the tubing 95 against the first distal end 232b of the first flexible element 232. The tubing 95 of medical equipment can be released from the gap 236 by, for example, pushing the tubing 95 against the second distal end 234b of the second flexible element 234.

The invention claimed is:

1. A neonate incubator for positioning a neonate within a magnetic resonance imaging (MRI) device, the neonate incubator comprising:
   a proximal end and a distal end;
   a radio frequency (RF) shielding door coupled to the distal end, the RF shielding door to mate with a bore of the MRI device to provide RF shielding; and
   a RF channel that extends along an axis that is substantially parallel to a longitudinal axis of the neonate incubator from an interior chamber of the neonate incubator through the RF shielding door, the RF channel having a length to width ratio of at least 5 to 1, wherein the RF shielding and the RF channel prevent an external RF radiation from entering the bore of the MRI device and an RF radiation emitted by the MRI device from exiting the bore of the MRI device, wherein the RF channel is configured to enable a passage of tubing of medical equipment from the interior chamber of the neonate incubator to an environment that is external to the neonate incubator, and wherein the RF channel comprises:
   a first cylindrical shell having a first cutout in a longitudinal direction along the first cylindrical shell, the first cutout being positioned adjacent to an outer edge of the RF shielding door; and
   a second cylindrical shell positioned coaxially within the first cylindrical shell, the second cylindrical shell having a second cutout in a longitudinal direction along the second cylindrical shell and a substantially hollow interior, the second cylindrical shell configured to rotate around a longitudinal axis of the second cylindrical shell.

2. The neonate incubator of claim 1, wherein the second cutout of the second cylindrical shell is configured to be aligned with the first cutout of the first cylindrical shell to enable an insertion of the tubing of medical equipment within the substantially hollow interior of the second cylindrical shell via the first and the second cutouts.

3. The neonate incubator of claim 1, wherein the RF channel is configured to enclose the tubing of medical equipment upon shifting of the second cutout of the second cylindrical shell to a position that is substantially opposite with respect to the first cutout of the first cylindrical shell.

4. The neonate incubator of claim 1, wherein at least a portion of the RF channel is positioned within the interior chamber of the incubator.

5. The neonate incubator of claim 1, wherein at least a portion of the RF channel protrudes from the RF shielding door towards the external environment.

6. The neonate incubator of claim 1, wherein the RF channel is configured to enable an insertion of the tubing of medical equipment without detaching the tubing from any of the medical equipment ends.

7. The neonate incubator of claim 1, wherein the RF channel further comprises at least one holder to hold a position of the tubing of medical equipment passing through the RF channel.

8. The neonate incubator of claim 1, further comprising at least one holder connected to the RF shielding door to hold a position of the tubing of medical equipment.

9. A neonate incubator for positioning a neonate within a magnetic resonance imaging (MRI) device, the neonate incubator comprising:
   a proximal end and a distal end;
   a radio frequency (RF) shielding door coupled to the distal end, the RF shielding door to mate with a bore of the MRI device to provide RF shielding;
   a RF channel that extends along an axis that is substantially parallel to a longitudinal axis of the neonate incubator from an interior chamber of the neonate incubator through the RF shielding door, the RF channel having a length to width ratio of at least 5 to 1, wherein the RF shielding door and the RF channel prevent an external RF radiation from entering the bore of the MRI device and an RF radiation emitted by the MRI device from exiting the bore of the MRI device, and wherein the RF channel is configured to enable a passage of tubing of medical equipment from the interior chamber of the neonate incubator to an environment that is external to the neonate incubator; and
   at least one holder connected to the RF shielding door to hold a position of the tubing of medical equipment, wherein the at least one holder comprises:

a first flexible element having a first proximal end and a first distal end, the first flexible element is connected to the RF shielding door at the first proximal end;

a second flexible element having a second proximal end and a second distal end, the second flexible element is connected to the RF shielding door at the second proximal end; and a gap bounded by the first flexible element, the second flexible element and a portion of the RF shielding door between the first and second proximal ends.

10. The neonate incubator of claim 9, wherein at least a portion of the first distal end of the first flexible element end overlaps with at least a portion of the second distal end of the second flexible element forming thereby a first overlapping portion and a second overlapping portion.

11. The neonate incubator of claim 10, wherein the first overlapping portion is closer to the RF shielding door than the second overlapping portion.

12. The neonate incubator of claim 11, wherein the tubing of medical equipment is positioned within the gap by pushing the tubing of medical equipment against the first distal end of the first flexible element and wherein the tubing of medical equipment is released from the gap by pushing the tubing of medical equipment against the second distal end of the second flexible element.

13. The neonate incubator of claim 10, wherein the second overlapping portion is closer to the RF shielding door than the first overlapping portion.

14. The neonate incubator of claim 13, wherein the tubing of medical equipment is positioned within the gap by pushing the tubing of medical equipment against the second distal end of the second flexible element and wherein the tubing of medical equipment is released from the gap by pushing the tubing of medical equipment against the first distal end of the first flexible element.

15. The neonate incubator of claim 13, wherein the first and second flexible elements have a substantially L-shape.

* * * * *